(12) United States Patent  (10) Patent No.: US 7,488,728 B2
Clark et al.  (45) Date of Patent: Feb. 10, 2009

(54) PYRIDINYLMORPHOLINE DERIVATIVES

(75) Inventors: Barry Peter Clark, Basingstoke (GB); Peter Thaddeus Gallagher, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 550 days.

(21) Appl. No.: 10/567,639

(22) PCT Filed: Aug. 9, 2004

(86) PCT No.: PCT/US2004/022313

§ 371 (c)(1),
(2), (4) Date: Feb. 8, 2006

(87) PCT Pub. No.: WO2005/023802

PCT Pub. Date: Mar. 17, 2005

(65) Prior Publication Data

US 2006/0258654 A1  Nov. 16, 2006

(30) Foreign Application Priority Data

Aug. 22, 2003  (GB) .................. 0319693.6

(51) Int. Cl.
*A61K 31/5377* (2006.01)
*C07D 413/12* (2006.01)
(52) U.S. Cl. ............... 514/237.2; 544/106; 544/111; 544/124; 514/231.2; 514/231.5; 514/235.5
(58) Field of Classification Search ............... 544/106, 544/111, 124; 514/231.2, 231.5, 235.5, 237.2
See application file for complete search history.

(56) References Cited

U.S. PATENT DOCUMENTS 7,294,623 B2 * 11/2007 Clark et al. ............... 514/239.2

FOREIGN PATENT DOCUMENTS

| GB | 2 060 622 A | 5/1981 |
| GB | 2 167 407 A | 5/1986 |
| WO | WO 99/15177 A | 4/1999 |
| WO | WO 00/39091 A | 7/2000 |
| WO | WO 01/01973 A | 1/2001 |
| WO | WO 03/106441 A | 12/2003 |
| WO | WO 2004/017977 A | 3/2004 |
| WO | WO 2004/018440 A | 3/2004 |

OTHER PUBLICATIONS

International Search Report.
Thornber C.W., "Isosterism and Molecular Modification in Drug Design", *Chemical Society Reviews*, vol. 8, No. 4, 1979, pp. 563-580.

* cited by examiner

*Primary Examiner*—Golam M Shameem
(74) *Attorney, Agent, or Firm*—Charles E. Cohen

(57) ABSTRACT

The invention relates to compounds of formula (I):

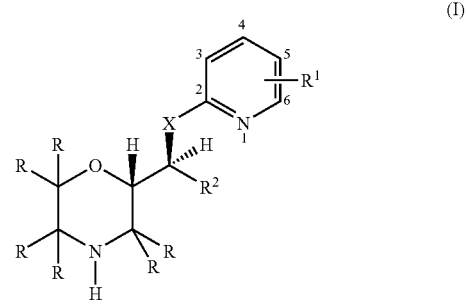

wherein R, $R^1$, $R^2$ and X are defined herein, their preparation, and their use as pharmaceuticals.

15 Claims, No Drawings

PYRIDINYLMORPHOLINE DERIVATIVES

This invention relates to novel morpholine compounds, and to their use in selectively inhibiting norepinephrine reuptake.

Selective inhibition of norepinephrine reuptake is a relatively new mode of action for the treatment of affective disorders. Norepinephrine appears to play an important role in the disturbances of vegetative function associated with affective, anxiety and cognitive disorders. Atomoxetine hydrochloride is a selective inhibitor of norepinephrine reuptake, and is marketed for the treatment of attention deficit hyperactivity disorder (ADHD). Reboxetine is also a selective norepinephrine reuptake inhibitor and is marketed for the treatment of depression. WO99/15177 discloses the use of Reboxetine to treat ADHD and WO01/01973 discloses the use of S,S-Reboxetine to treat ADHD.

According to the present invention there is provided a compound of formula (I)

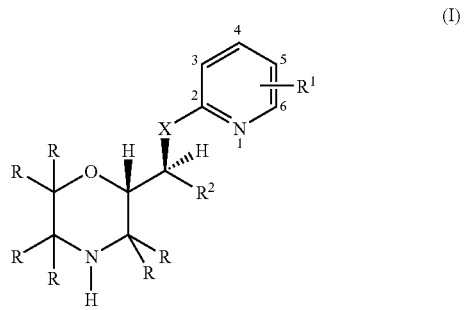

wherein
—X— is —S— or —O—;
each R is independently selected from H or $C_1$-$C_4$ alkyl;
$R^1$ is H, $C_1$-$C_4$ alkyl, $C_1$-$C_4$ alkoxy, halo, cyano, trifluoromethyl, trifluoromethoxy, —$NR^3R^4$, —$CONR^3R^4$, —$COOR^3$ or a group of the formula (i)

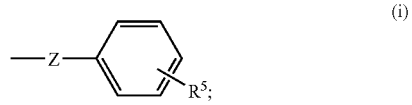

$R^2$ is $C_1$-$C_4$ alkyl, phenyl or phenyl substituted with 1, 2 or 3 substituents each independently selected from $C_1$-$C_4$ alkyl, $C_1$-$C_4$ alkoxy, nitro, hydroxy, cyano, halo, trifluoromethyl, trifluoromethoxy, benzyl, benzyloxy, —$NR^6R^7$, —$CONR^6R^7$, $COOR^6$, —$SO_2NR^6R^7$ and —$SO_2R^6$;
$R^5$ is selected from H, $C_1$-$C_4$ alkyl, $C_1$-$C_4$ alkoxy, carboxy, nitro, hydroxy, cyano, halo, trifluoromethyl, trifluoromethoxy, benzyl, benzyloxy, —$NR^8R^9$, —$CONR^8R^9$, —$SO_2NR^8R^9$ and —$SO_2R^8$;
$R^3$, $R^4$, $R^6$, $R^7$, $R^8$ and $R^9$ are each independently selected from H or $C_1$-$C_4$ alkyl; and
-Z- is a bond, —$CH_2$—, or —O—;
or a pharmaceutically acceptable salt thereof.

In the present specification the term "$C_1$-$C_4$ alkyl" means a monovalent unsubstituted saturated straight-chain or branched-chain hydrocarbon radical having from 1 to 4 carbon atoms. Thus the term "$C_1$-$C_4$ alkyl" includes methyl, ethyl, n-propyl, isopropyl, n-butyl, isobutyl, sec-butyl and tert-butyl.

In the present specification the term "$C_1$-$C_4$ alkoxy" means a monovalent unsubstituted saturated straight-chain or branched-chain hydrocarbon radical having from 1 to 4 carbon atoms linked to the point of substitution by an O atom. Thus the term "$C_1$-$C_4$ alkoxy" includes methoxy, ethoxy, n-propoxy, isopropoxy, n-butoxy, isobutoxy, sec-butoxy and tert-butoxy.

In the present specification the term "halo" or "halogen" means F, Cl, Br or I.

In a preferred embodiment of the present invention —X— is —S—.

In another preferred embodiment of the present invention —X— is —O—.

In another preferred embodiment of the present invention $R^2$ is phenyl.

In another preferred embodiment of the present invention all R groups are hydrogen.

A preferred group of compounds according to the present invention is represented by the formula (II)

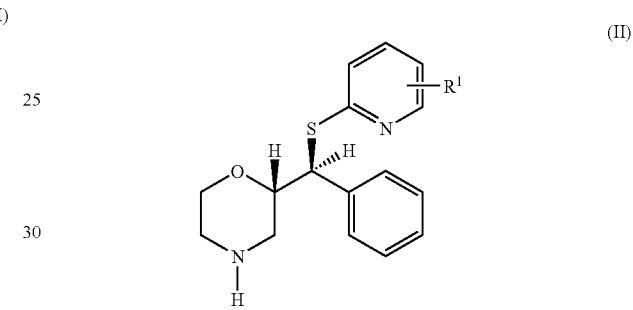

wherein $R^1$ is H, $C_1$-$C_4$ alkyl, $C_1$-$C_4$ alkoxy, halo, cyano, trifluoromethyl, trifluoromethoxy, —$NR^3R^4$, —$CONR^3R^4$, —$COOR^3$ or a group of the formula (i)

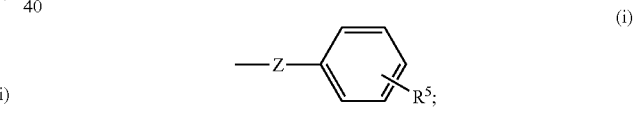

$R^5$ is selected from H, $C_1$-$C_4$ alkyl, $C_1$-$C_4$ alkoxy, carboxy, nitro, hydroxy, cyano, halo, trifluoromethyl, trifluoromethoxy, benzyl, benzyloxy, —$NR^8R^9$, —$CONR^8R^9$, —$SO_2NR^8R^9$ and —$SO_2R^8$;
$R^3$, $R^4$, $R^8$ and $R^9$ are each independently selected from H or $C_1$-$C_4$ alkyl;
-Z- is a bond, —$CH_2$—, or —O—;
or a pharmaceutically acceptable salt thereof.

A preferred embodiment of the present invention relates to compounds of formula (I) or (II) wherein the substituent $R^1$ is in the three position of the pyridine ring as numbered in formula (I) above.

More preferably said substituent $R^1$ is H, $C_1$-$C_4$ alkyl, halo, cyano, —$CONR^3R^4$, trifluoromethyl or a group of the formula (i).

When $R^1$ is —$CONR^3R^4$, then $R^3$ and $R^4$ are both preferably H.

When $R^1$ is $C_1$-$C_4$ alkyl, then it is preferably methyl.

A preferred embodiment of the present invention relates to compounds of formula (I) or (II) wherein the substituent $R^1$ is a group of the formula (i).

Another preferred embodiment of the present invention relates to compounds of formula (I) or (II) wherein $R^1$ is a group of the formula (i), -Z- is a bond, and $R^5$ is H or halo.

Another preferred embodiment of the present invention relates to compounds of formula (I) or (II) wherein $R^1$ is a group of the formula (i), -Z- is —$CH_2$— or —O—, and $R^5$ is H.

Another preferred embodiment of the present invention relates to compounds of formula (I) or (II) wherein the substituent $R^1$ is in the five position of the pyridine ring as numbered in formula (I) above. More preferably said substituent $R^1$ is selected from bromo, chloro or iodo.

The present invention includes the pharmaceutically acceptable salts of the compounds of formula (I) or formula (II). Suitable salts include acid addition salts, including salts formed with inorganic acids, for example hydrochloric, hydrobromic, nitric, sulphuric or phosphoric acids, or with organic acids, such as organic carboxylic or organic sulphonic acids, for example, acetoxybenzoic, citric, glycolic, mandelic-1, mandelic-d1, mandelic-d, maleic, mesotartaric monohydrate, hydroxymaleic, fumaric, lactobionic, malic, methanesulphonic, napsylic, naphthalenedisulfonic, naphtoic, oxalic, palmitic, phenylacetic, propionic, pyridyl hydroxy pyruvic, salicylic, stearic, succinic, sulfanilic, tartaric-1, tartaric-d1, tartaric-d, 2-hydroxyethane sulphonic, toluene-p-sulphonic, and xinafoic acids.

In addition to the pharmaceutically acceptable salts, other salts may serve as intermediates in the purification of compounds or in the preparation of other, for example pharmaceutically acceptable, acid addition salts, or are useful for identification, characterisation or purification.

It will be appreciated that compounds of formula (I) and formula (II) possess asymmetric carbon atoms, and that in the present invention specific individual stereoisomers are preferred. In the present specification, where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers.

Compounds of the present invention may be prepared by conventional organic chemistry techniques from N-protected-2-cyanomorpholines as outlined in Scheme 1 below, wherein R and $R^2$ have the values defined for formula (I) above and P is a suitable nitrogen protecting group such as those described in T. W. Greene, "Protective Groups in Organic Synthesis", John Wiley and Sons, New York, N.Y., 1991, hereafter referred to as "Greene". For example a suitable nitrogen protecting group is a benzyl group:

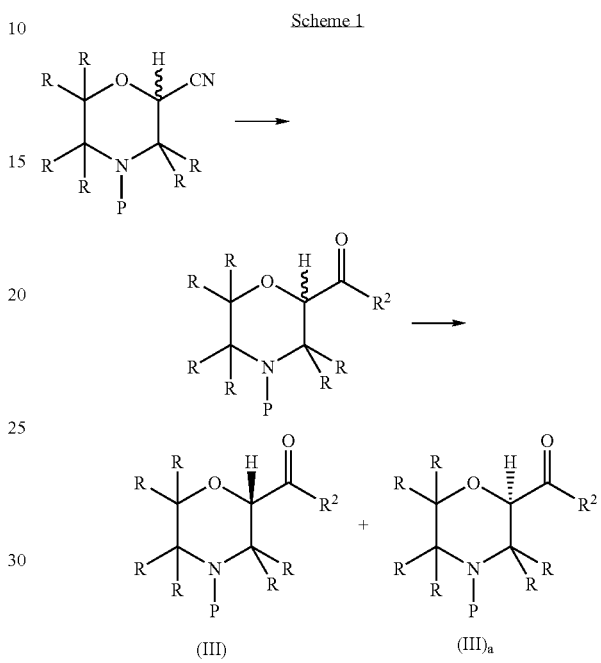

Scheme 1

The phenyl ketone (III) can be obtained by reaction of N-protected-2-cyanomorpholine with a Grignard reagent, followed by acid hydrolysis to give the racemic phenyl ketone which may be separated on chiral HPLC.

Compounds of formula (I) wherein —X— is —S— can be prepared from the N-protected morpholine ketone intermediate of formula (III), as illustrated in Scheme 2 below:

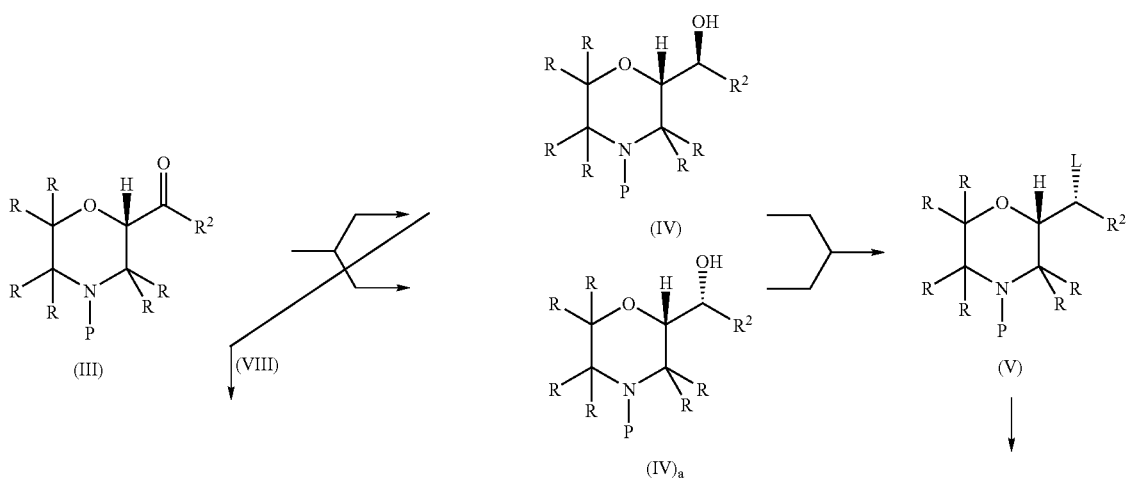

Scheme 2

-continued

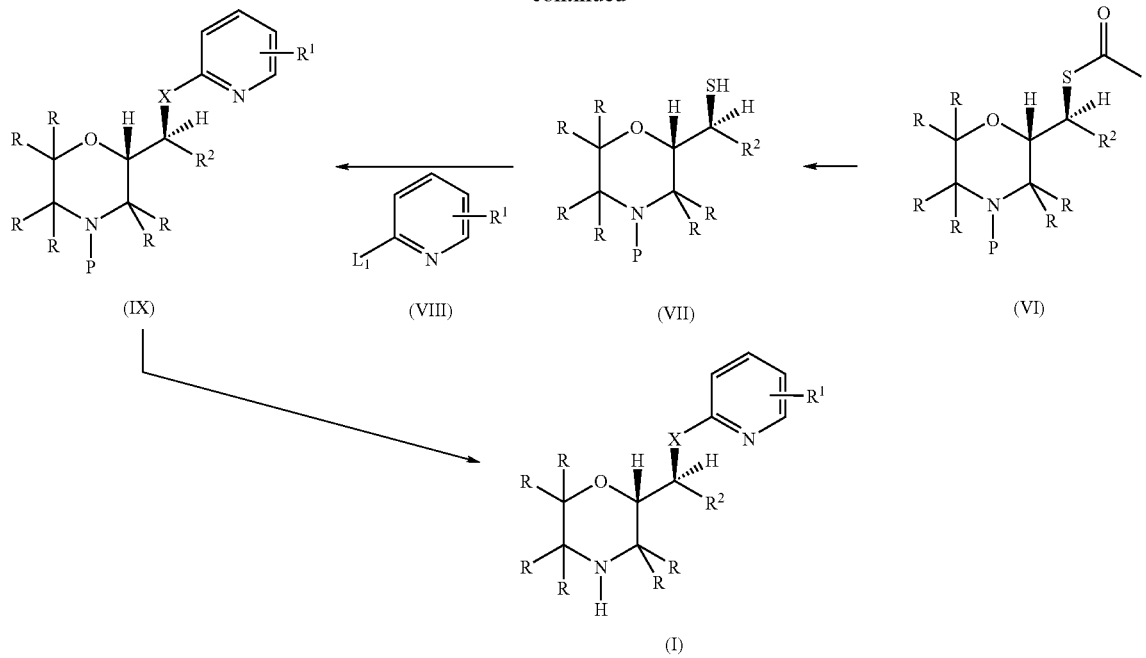

The ketone is stereoselectively reduced to the corresponding (2S) or (2R) alcohol of formula (IV) or (IV)$_a$ using standard methods known in the art. For example it can be reduced in the presence of [(−)-B-chlorodiisopinocampheylborane] in a suitable solvent such as tetrahydrofuran (THF) to provide the (2S) alcohol.

The resulting alcohol is then transformed into a suitable leaving group L. Suitable leaving groups include halo groups, such as bromo, chloro or iodo and sulfonate groups, such as mesylate. When L is a halo group, the alcohol used will be the (2S) enantiomer (IV) and it will be reacted with inversion of stereochemistry. For example, when L is bromo, the bromination reaction can be carried out in the presence of a brominating agent such as triphenylphosphine dibromide, in a suitable solvent such as chloroform. When L is a mesylate group, the alcohol used will be the (2R) enantiomer (IV)$_a$ and it will be reacted with retention of stereochemistry in the presence of mesylate chloride and a suitable base.

The resulting intermediate of formula (V) can then be converted into the corresponding methylethanethioate of formula (VI) via displacement of the leaving group with a suitable thiolacetate salt such as potassium thiolacetate in the presence of a suitable solvent such as a mixture of dimethylformamide (DMF) and tetrahydrofuran (THF).

The methanethiol intermediate of formula (VII) can be prepared via reaction of the methylethanethioate (VI) with a suitable thiomethoxide such as sodium thiomethoxide in the presence of a suitable solvent such as methanol (one can use a variety of bases but thiomethoxide is preferred because it also acts as a reducing agent and prevents oxidation of thiol hence inhibiting dimerisation; Ref: O. B. Wallace & D. M. Springer, *Tetrahedron Letters*, 1998, 39 (18), pp2693-2694).

The pyridyl portion of the molecule is incorporated via general methods known in the art. A particularly useful method is the reaction of the methanethiol (VII) with a compound of the formula

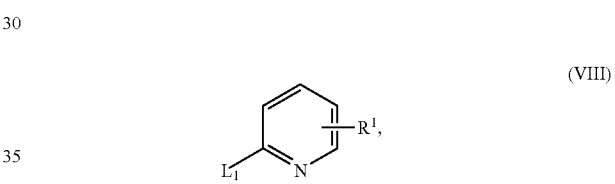

wherein R$^1$ has the values defined above and L$_1$ is a suitable leaving group such as fluoro, bromo, chloro, iodo or mesylate, in the presence of suitable base such as sodium hydride, cesium fluoride or sodium methoxide, in a suitable solvent such as DMF.

Compounds of formula (I) wherein —X— is —O— can be prepared in an analogous fashion by reaction of the (2S) alcohol of formula (IV) with a compound of formula (VIII) above.

The final step for the preparation of compounds of formula (I) comprises deprotection of the morpholine ring. Conditions for the deprotection depend on the protecting group chosen. Suitable deprotecting conditions can be found in Greene. For example when the nitrogen protecting group is a benzyl group, the deprotection reaction can be carried out in the presence of polymer supported diisopropylamine (PS-DIEA) and 1-chloroethyl chloroformate (ACE-Cl) in a suitable solvent such as dichloromethane, followed by reaction with methanol to give compounds of formula (I).

Compounds of formula (I) can alternatively be prepared by the derivatisation of a suitable substituent in the pyridyl ring to give the desired substituent R$^1$ as shown in Scheme 3 below. For example compounds of formula (I) wherein —R$^1$ is —CF$_3$ can be prepared via reaction of the intermediate (IX)' wherein L$_2$ is introduced into the molecule in place of R$^1$ in formula (VIII) as shown in Scheme 2 above. The group L$_2$ is a suitable leaving group such as for example iodo, bromo, chloro or fluoro. The leaving group is converted into a trifluoromethyl group via reaction in the presence of copper iodide, a suitable base such as for example potassium fluoride, and a suitable source of a trifluoromethyl group such as for example (trifluoromethyl)trimethylsilane, in a suitable solvent such as for example a mixture of DMF and N-methylpyrrolidinone (NMP). The resulting compound of formula (X) is deprotected using the methodology described above.

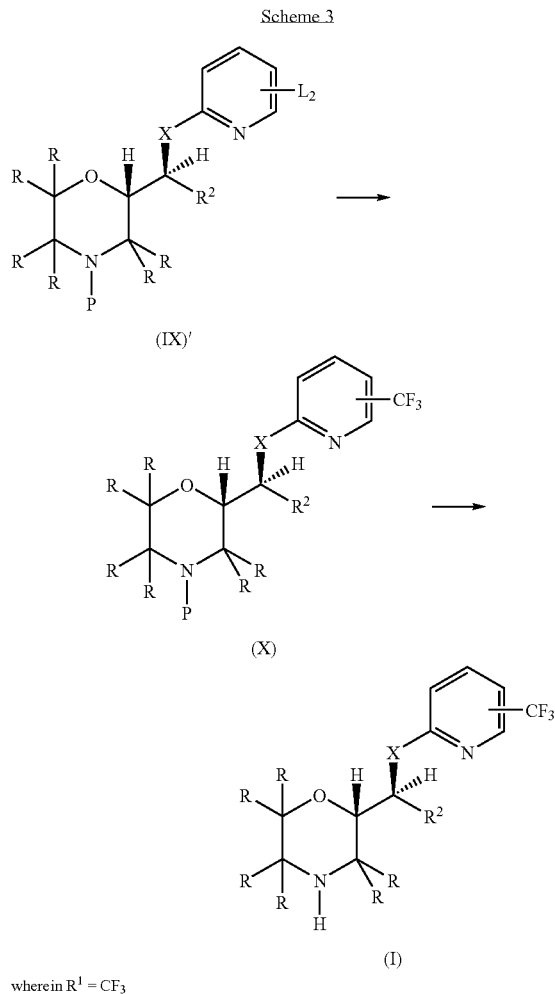

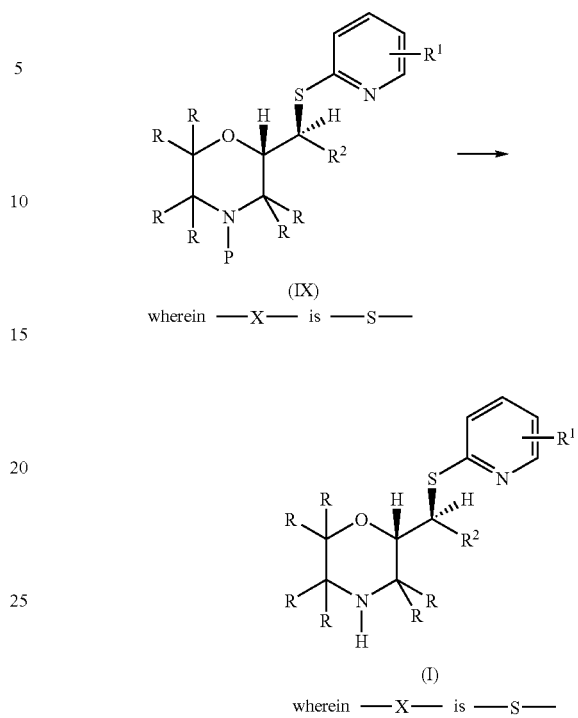

wherein —X— is —S— wherein —X— is —S—

The reaction can be carried out via general methods known in the art. For example, the intermediate (VI) can be reacted with a compound of formula (VIII), wherein $R^1$ and $L_1$ have the values defined above, in the presence of a suitable base such as sodium methoxide, in a suitable solvent such as for example DMF.

The resulting compound of formula (IX) wherein —X— is —S— is then deprotected using the methods described above for Scheme 2 to give a compound of formula (I) wherein —X— is —S—. This method is particularly useful when $L_1$ and $R^1$ are halogen groups such as for example fluoro and bromo respectively. Alternatively, the reaction can be carried out in the presence of a suitable base such as sodium hydroxide in a suitable solvent such as a mixture of ethanol and water. This method is particularly useful when $L_1$ is a halogen group and —$R^1$ is —CN or —CONR$^3$R$^4$, wherein $R^3$ and $R^4$ have the values defined for formula (I) above.

Compounds of formula (I) wherein —X— is —S— can also be prepared via an alternative method using the intermediate of formula (V) as illustrated below in Scheme 5.

Compounds of formula (I) wherein —X— is —S— can alternatively be prepared directly from the intermediate methylethanethioate of formula (VI) as illustrated in Scheme 4 below.

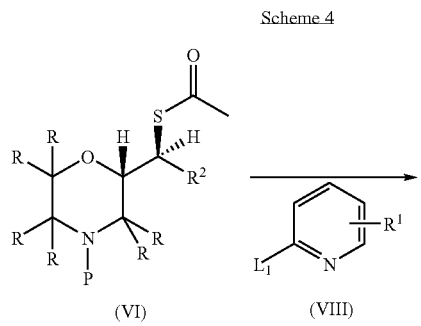

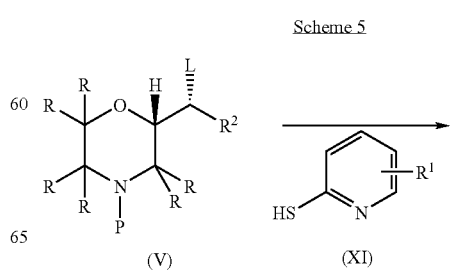

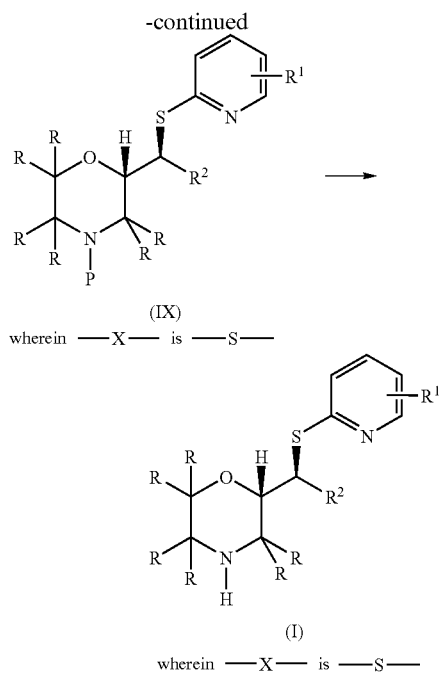

(IX)
wherein —X— is —S—

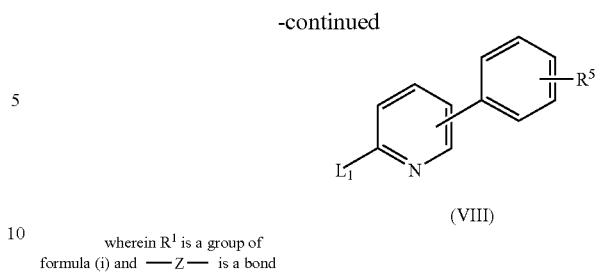

(VIII)

wherein $R^1$ is a group of formula (i) and —Z— is a bond

The reaction is carried out via reaction of readily available pyridines of formula (XII) wherein $L_1$ has the values mentioned above and $L_3$ is a suitable leaving group such as for example a halogen group such as bromo or chloro, with the corresponding phenylboronic acid of formula (XIII), in the presence of a suitable palladium catalyst such as for example palladium acetate, a suitable ligand such as triphenylphosphine, in a suitable solvent such as acetonitrile. Alternative palladium catalysts are known in the art, for example bis(benzonitrile)palladium(II)dichloride can be used in the presence of a suitable ligand such as for example bis(diphenylphosphine)butane and a suitable base such as sodium carbonate in a suitable solvent such as for example ethanol, to give good yields of intermediate of formula (VIII) wherein $R^1$ is a group of formula (i) and -Z- is a bond.

Intermediates of formula (VIII) wherein $R^1$ is a group of formula (i) and -Z- is —$CH_2$— can be prepared by the method illustrated in Scheme 7 below.

(I)
wherein —X— is —S—

The leaving group of intermediate (V) is displaced with a suitable thiol of formula (XI) wherein $R^1$ has the values defined for formula (I) above, in the presence of a suitable base such as potassium carbonate, in a suitable solvent such as DMF. The resulting intermediate of formula (IX) wherein —X— is —S— is then deprotected as described in Scheme 2 above.

The intermediate of formula (VIII) above (including analogs wherein $L_2$ is introduced in place of $R^1$) often commercially available. This is the case for intermediates wherein $L_1$ is a halogen group and $R^1$ (or $L_2$) has the values selected from H, methyl, halo, cyano, trifluoromethyl, $NH_2$, $CO_2H$, $CONH_2$, $SO_2H$, $SO_2NHCH_3$, $NCOCCl_3$ and $NSO_2Ph$.

Intermediates of formula (VIII) wherein $R^1$ is a group of formula (i) can readily be prepared via methods known in the art. We illustrate below 3 methods for the preparation of compounds of formula (VIII) wherein $R^1$ is a group of formula (i) and -Z- has the value of a bond (Scheme 6), —$CH_2$— (Scheme 7) or —O— (Scheme 8).

It will be appreciated that these methods are only illustrative as there are many other alternative methods known in the art which can be used.

As mentioned above, intermediates of formula (VIII) wherein $R^1$ is a group of formula (i) and -Z- is a bond can be prepared via palladium coupling as illustrated in Scheme 6 below.

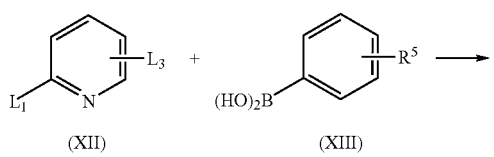

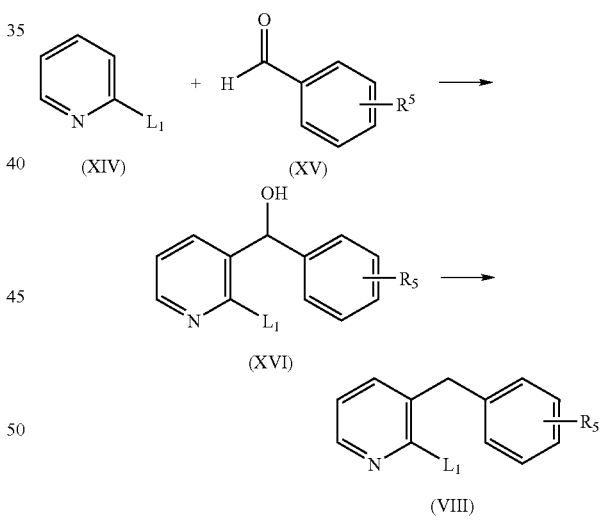

wherein $R^1$ is a group of formula (i) and —Z— is —$CH_2$—

Readily available pyridine compounds of formula (XIV) wherein $L_1$ has the values mentioned above (preferably fluoro) are reacted with suitable benzaldehydes of formula (XV), wherein $R^5$ has the value defined for formula (I) above, in the presence of a suitable base such as for example n-butyllithium or lithium diisopropylamide, in a suitable solvent such as THF, to give the alcohol of formula (XVI). Said alcohol is then reduced to give the corresponding benzyl derivative (VIII) wherein $R^1$ is a group of formula (i) and -Z- is —$CH_2$— via hydrogenation, in the presence of a suitable catalyst such as for example palladium on charcoal, in a suitable solvent such as for example ethanol.

Intermediates of formula (VIII) wherein $R^1$ is a group of formula (i) and -Z- is —O— can be prepared by the method illustrated below in Scheme 8.

Scheme 8

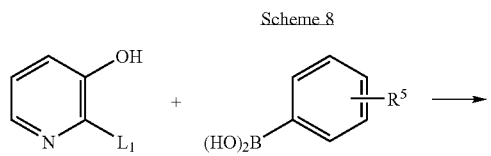

(XVII)     (XIII)

wherein $R^1$ is a group of formula (i) and
—Z— is —O—

Readily available pyridinols of formula (XVII), wherein $L_1$ has the values mentioned above react with phenylboronic acids of formula (XIII) in the presence of copper(II)acetate, powdered 4 Å molecular sieves, and a suitable base such as triethylamine, in a suitable solvent such as for example dichloromethane to give intermediates of formula (VIII) wherein $R^1$ is a group of formula (i) and -Z- is —O—.

Compounds of formula (1) wherein —X— is —O— may also be prepared by conventional chemistry techniques from the (2R) alcohol $(IV)_a$ using standard methods known in the art. For example as shown in Scheme 9 by reaction of said alcohol with a pyridine of the formula (XVIII) or the ketone tautomer of this pyridine wherein $R^1$ has the values defined for formula (I) above, in the presence of a suitable phosphine such as triphenyl phosphine and diethyl azodicarboxylate, using an appropriate solvent such as THF, dimethoxyethane, (DME), or chloroform (CHCl$_3$), as described by D. L. Comins and G. Jianhua, in *Tetrahedron Letters*, 1994, 35 (18), pp2819-2822. This reaction is usually carried out with inversion of the stereocentre to (2S)

Scheme 9

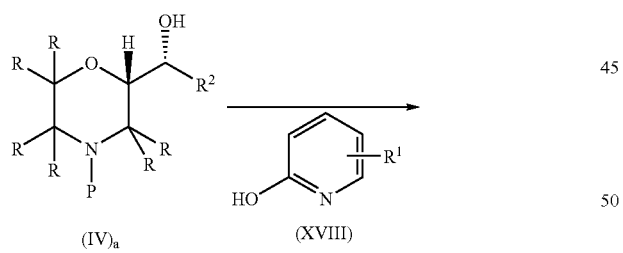

(I)

wherein —X— is —O—

As previously mentioned, compounds of formula (I) wherein —X— is —O— may alternatively be prepared by the reaction of the (2S) alcohol (IV) with a pyridine of the formula (VIII), where $L_1$ is preferably chloro and $R^1$ has the values defined for formula (I) above, using a suitable base such as potassium hydroxide, in a suitable solvent such as benzene or toluene, in the presence of a suitable phase transfer catalyst such as 18-Crown-6 as described by A. J. S. Duggan et al, in *Synthesis*, 1980, 7, p573.

Scheme 10

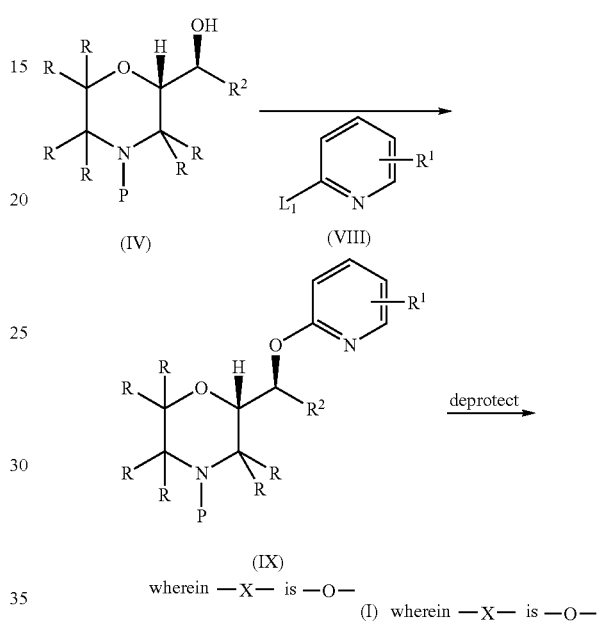

wherein —X— is —O—

(I) wherein —X— is —O—

Compounds of formula (I) wherein —X— is —O— may alternatively be prepared by the reaction of intermediate (V) wherein L is Br with a pyridine of the formula (VIII) wherein -$L_1$ is —OAg and $R^1$ has the values defined for formula (I) above, in a non-polar solvent such as benzene, as described by U. Schollkopf et al, in *Liebigs Ann. Chem.* 1972, 765, pp153-170 and G. C. Hopkins et al, in *J. Org. Chem.* 1967, 32, pp4040.

The present invention also provides a process for producing a compound of formula (I) above, which comprises deprotecting a compound of the formula (IX)

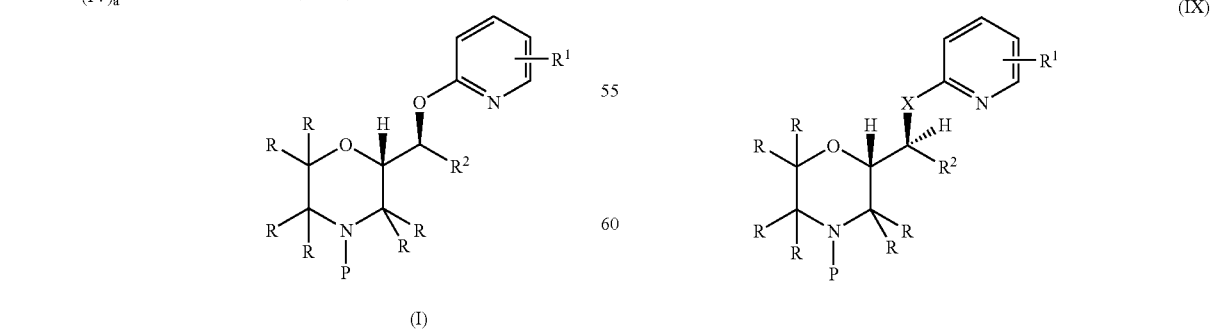

where P is an N-protecting group, optionally followed by the further step of forming a pharmaceutically salt. Suitable N-protecting groups will be known to the person skilled in the art and as described in, for example, Greene. They include, for example, benzyl, benzyloxycarbonyl (boc) and acetyl.

Compounds of the present invention are norepinephrine reuptake inhibitors and are selective over other neurotransmitters, such as dopamine or serotonin. That is their binding affinity at the norepinephrine transporter is higher than their affinity for other transporters or other receptors. Preferably the compounds of the present invention selectively inhibit the reuptake of the norepinephrine transporter relative to the serotonin and dopamine transporters by a factor of at least five, and even more preferably by a factor of at least ten. Compounds of formula (I) and their pharmaceutically acceptable salts preferably exhibit a $K_i$ value less than 500 nM at the norepinephrine transporter as determined using the scintillation proximity assay as described below. More preferred compounds of formula (I) and their pharmaceutically acceptable salts exhibit a $K_i$ value less than 100 nM at the norepinephrine transporter. More preferred compounds of formula (I) and their pharmaceutically acceptable salts exhibit a $K_i$ value less than 50 nM at the norepinephrine transporter. Especially preferred compounds of formula (I) and their pharmaceutically acceptable salts exhibit a $K_i$ value less than 20 nM at the norepinephrine transporter. In addition, they are preferably acid stable. Advantageously, they also have a reduced interaction (both as substrate and inhibitor) with the liver enzyme Cytochrome P450 (CYP2D6) compared with other norepinephrine-reuptake inhibitors, such as reboxetine. That is to say, they preferably exhibit less than 75% metabolism via the CYP2D6 pathway according to the CYP2D6 substrate assay described below and they preferably exhibit an IC50 of >6 μM according to the CYP2D6 inhibitor assay described below.

Thus, the present invention provides a compound of formula (I), or a pharmaceutically acceptable salt thereof, for use as a selective inhibitor of the reuptake of norepinephrine. Preferably such selective inhibition occurs within mammalian cells (including mammalian cell membrane preparations), especially those found within the central and/or peripheral nervous system. More preferably such selective inhibition occurs within the cells of the central nervous system of a mammal, especially a human, in need thereof. Thus, the present invention also provides a compound of formula (I), or a pharmaceutically acceptable salt thereof, for use in therapy. In particular, the present invention provides a compound of formula (I), or a pharmaceutically acceptable salt thereof, for treating disorders associated with norepinephrine dysfunction in mammals, including the disorders listed herein.

The present invention also provides for the use of a compound of formula (I), or a pharmaceutically acceptable salt thereof, for selectively inhibiting the reuptake of norepinephrine; and the use of a compound of formula (I), or a pharmaceutically acceptable salt thereof, for the treatment of disorders associated with norepinephrine dysfunction in mammals, including the disorders listed herein.

The present invention also provides for the use of a compound of formula (I), or a pharmaceutically acceptable salt thereof, for the manufacture of a medicament for selectively inhibiting the reuptake of norepinephrine; and the use of a compound of formula (I), or a pharmaceutically acceptable salt thereof, for the manufacture of a medicament for the treatment of disorders associated with norepinephrine dysfunction in mammals, including the disorders listed herein.

Further, the present invention provides a method for selectively inhibiting the reuptake of norepinephrine in mammals, comprising administering to a patient in need thereof an effective amount of a compound of formula (I), or a pharmaceutically acceptable salt thereof; and a method for treating disorders associated with norepinephrine dysfunction in mammals, comprising administering to a patient in need thereof an effective amount of a compound of formula (I), or a pharmaceutically acceptable salt thereof.

The term "norepinephrine dysfunction" as used herein refers to a reduction in the amount of norepinephrine neurotransmitter within the synaptic cleft below that which would be considered to be normal, or desirable, for an individual within that species. Thus the phrase "disorders associated with norepinephrine dysfunction in mammals" refers to disorders which are associated with a reduction in the amount of norepinephrine neurotransmitter within the synaptic cleft below that which would be considered to be normal, or desirable, for the mammalian species, or an individual within that species, in question. Some examples of disorders currently believed to be associated with reduced levels of norepinephrine within the synaptic cleft are detailed below.

The compounds of the present invention are also indicated for the treatment of disorders which are ameliorated by an increase in the amount of norepinephrine neurotransmitter within the synaptic cleft of a mammal above that which would be considered to be normal, or desirable for the mammalian species or an individual within that species, in question.

The term "treatment" as used herein refers to both curative and prophylactic treatment of disorders associated with norepinephrine dysfunction.

Disorders associated with norepinephrine dysfunction in mammals, mentioned above in either the uses or the methods of the present invention, include, for example, nervous system conditions selected from the group consisting of an addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, allergies, anorexia nervosa, apathy, asthma, an attention-deficit disorder (ADD) due to general medical conditions, attention-deficit hyperactivity disorder (ADHD) including the predominantly inattentive type of ADHD and the predominantly hyperactive-impulsive type of ADHD (and optionally by way of combination therapy with one or more stimulants such as methylphenidate, amphetamine and dextroamphetamine), bipolar disorder, bulimia nervosa, chronic fatigue syndrome, chronic or acute stress, cognitive disorders (discussed in more detail below but including mild cognitive impairment (MCI) and cognitive impairment associated with schizophrenia (CIAS)), communication disorders (including stuttering, expressive language disorder, mixed receptive-expressive language disorder, phonological disorder and communication disorder not otherwise specified), conduct disorder, cyclothymic disorder, dementia of the Alzheimers type (DAT), depression (including adolescent depression and minor depression), dysthymic disorder, emotional dysregulation (including emotional dysregulation associated with ADHD, borderline personality disorder, bipolar disorder, schizophrenia, schizoaffective disorder and intermittent explosive disorder), fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder, hot flashes or vasomotor symptoms, hypotensive states including orthostatic hypotension, impulse control disorders (including intermittent explosive disorder, kleptomania, pyromania, pathological gambling, trichotillomania and impulse-control disorder not otherwise specified), incontinence (i.e. bedwetting, stress incontinence, genuine stress incontinence, and mixed incontinence), an inhalation disorder, an intoxication disorder, learning disabilities (including developmental speech and language disorders (such as developmental articulation disorder, developmental expressive language disorder and developmental receptive language disorder), learning disorders (such as reading disorder, mathematics disorder, disorder of written expression and learning disorder not otherwise specified) and motor skills disorders (such as developmental coordination disorder)), mania, migraine headaches, neuropathic pain, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, Parkinson's disease (in particular to improve dyskinesia, oscilations, balance, coordination, depression, and motivation), peripheral neuropathy, personality change due to a general medical condition (including labile type, disinhibited type, aggressive type, apathetic type, paranoid type, combined type and unspecified type), pervasive developmental disorders (including autistic disorder, Asperger's disorder, Rett's disorder, childhood disintegrative disorder, and pervasive developmental disorder not otherwise specified), post-traumatic stress disorder, premenstrual dysphoric disorder (i.e., premenstrual syndrome and late luteal phase dysphoric disorder), psoriasis, psychoactive substance use disorders, a psychotic disorder (including schizophrenia, schizoaffective and schizophreniform disorders), seasonal affective disorder, a sleep disorder (such as narcolepsy and enuresis), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), tobacco addiction and vascular dementia. They are most particularly useful for the treatment of ADHD.

The term "cognitive disorders" (also variously referred to as "cognitive failure," "cognitive insufficiency," "cognitive deficit," "cognitive impairment," "cognitive dysfunction," and the like) refers to the dysfunction, diminution, or loss of one or more cognitive functions, the processes by which knowledge is acquired, retained, and used. Cognitive dysfunction includes cognitive changes associated with ageing ("age-associated memory impairment"), as well as changes due to other causes. Cognitive impairment is most commonly due to a delirium or dementia, but can also occur in association with a number of other medical or neuropsychiatric disorders. More focal cognitive deficits are diagnosed using the criteria disclosed in the *Diagnostic and Statistical Manual of Mental Disorders*, Fourth Edition, Text Revision (DSM-IV-TR™, 2000), American Psychiatric Association, Washington, D.C., as either amnestic disorders (affecting memory) or cognitive disorder not otherwise specified (NOS), which includes executive dysfunction, visuospatial/visuocontructional impairment, attentional deficits, disorientation, etc. These more focal cognitive disorders also have a wide variety of causes, some of which are of unknown etiology.

A delerium is characterized by a disturbance of consciousness with a reduced ability to focus, sustain, or shift attention and a change in cognition that develops over a short period of time. Delirium is very common, and occurs on average in about a fifth of general hospital inpatients, and is even more common in nursing home patients and those with terminal illnesses. The disorders included in the "Delirium" section of the DSM-IV-TR™ are listed according to presumed etiology: Delirium Due to a General Medical Condition, Substance-Induced Delirium (i.e., due to a drug of abuse, a medication, or toxin exposure), Delirium Due to Multiple Etiologies, or Delirium Not Otherwise Specified (if the etiology is indeterminate). As disclosed by Wise et al. ((2002) Delirium (Confusional States), In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 15, pp. 257-272, Table 15-4), exemplary etiological bases of delirium include, but are not limited to, infection, withdrawal from alcohol and drugs, acute metabolic conditions, trauma of various types, CNS pathologies, hypoxia, vitamin deficiencies, endocrinopathies, acute vascular conditions, toxins or drugs, and heavy metals.

A dementia is a chronic condition, usually with a more gradual deterioration of memory and other intellectual functioning and other cognitive skills severe enough to interfere with the ability to perform activities of daily living. Although dementia may occur at any age, it primarily affects the elderly, presenting in more than 15% of persons over 65 years of age and in as many as 40% of persons over 80 years old. Dementia due to Alzheimer's disease is particularly common. Non-Alzheimer's cognitive impairments and/or dementias include, for example, those caused by or associated with: vascular diseases; Parkinson's disease; Lewy body disease (diffuse Lewy body disease); HIV/AIDS; mild cognitive impairments; mild nuerocognitive disorders; age-associated memory impairments; neurologic and/or psychiatric conditions including epilepsy and epilepsy treatments; brain tumors, cysts, lesions, or other inflammatory brain diseases; multiple sclerosis; Down's syndrome; Rett's syndrome; progressive supranuclear palsy; frontal lobe dementia syndromes; schizophrenia and related psychiatric disorders; antipsychotic medications; traumatic brain injury (closed head injury), dementia pugilistica, and other head traumas; normal-pressure hydrocephalus; surgery (including coronary artery by-pass graft surgery) and anaesthesia, electroconvulsive shock therapy, and cancer and cancer therapies.

The dementias are also listed in the "Dementia" section of the DSM-IV-TR™ according to presumed etiology: Dementia of the Alzheimer's Type, Vascular Dementia, Dementia Due to Other General Medical Conditions (e.g., human immunodeficiency virus [HIV] disease, head trauma, Parkinson's disease, Huntington's disease), Substance-Induced Persisting Dementia (i.e., due to a drug of abuse, a medication, or toxin exposure), Dementia Due to Multiple Etiologies, or Dementia Not Otherwise Specified (if the etiology is indeterminate). As disclosed by Gray and Cummings ((2002) Dementia, In Wise and Rundell, Eds., *The American Psychiatric Publishing Textbook of Consultation-Liaison Psychiatry, Psychiatry in the Medically Ill*, Second Edition, American Psychiatric Publishing, Inc., Washington, D.C., Chapter 16, pp. 273-306, Table 16-1), exemplary etiological bases of principal dementia syndromes include, but are not limited to, degenerative disorders (cortical and subcortical), vascular disorders, myelinoclastic disorders, traumatic conditions, neoplastic disorders, hydrocephalic disorders, inflammatory conditions, infections, toxic conditions, metabolic disorders, and psychiatric disorders.

An amnestic disorder is characterized by memory impairment in the absence of other significant accompanying cognitive impairments. The disorders in the "Amnestic Disorders" section of the DSM-IV-TR™ are also listed according to presumed etiology: Amnestic Disorder Due to a General Medical Condition, Substance-Induced Persisting Amnestic Disorder, or Amnestic Disorder Not Otherwise Specified.

Cognitive Disorder Not Otherwise Specified in the DSM-IV-TR™ covers presentations that are characterized by cognitive dysfunction presumed to be due to either a general medical condition or substance use that do not meet criteria for any of the disorders listed elsewhere in the section of the DSM-IV-TR™ entitled "Delirium, Dementia, and Amnestic and Other Cognitive Disorders."

Dementia, amnestic disorders, and cognitive disorders NOS occur in patients with a wide variety of other disorders including, but not limited to, Huntington's disease (chorea); Pick's disease; spinocerebellar ataxias (types 1-11); cortico-basalganglionic degeneration; neuroacanthocytosis; dentatorubropallidoluysian atropy (DRPLA); systemic lupus erythematosus; heavy metal intoxication; alcoholic dementia (Wernicke's encephalopathy); fetal alcohol syndrome; single or multiples strokes, including small vessels (Binswanger's dementia: subcortical arteriosclerotic encephalopathy) and large vessels (multi-infarct dementia); anoxic encephalopathy; tumors; birth anoxia; premature birth; inborn errors of metabolism; neurofibromatosis (Type I); tuberous sclerosis; Hallervorden Spatz disease; Wilson's disease; post-infectious sequelae (e.g., tuberculosis, viral encephalitis, bacterial meningitis); subdural hematoma; subcortical dementia; Creutzfeldt-Jakob disease; Gerstmann-Sträussler-Scheinker disease; general paresis; and syphilis.

As discussed in detail above, cognitive failure may present in patients suffering from a number of disorders, including dementia or delirium, or due to a wide variety of other causes. The compounds of the present invention are useful for the treatment or prevention of cognitive failure associated with, or due to, the disorders or etiologies discussed above, including disorders formally classified in the DSM-TV-TR™. For the convenience of the reader, the DSM-IV-TR™ code numbers or descriptions are supplied below. "ICD-9-CM codes" refers to codes for, e.g., selected general medical conditions and medication-induced disorders contained in the *International Classification of Diseases*, $9^{th}$ Revision, Clinical Modification.

| | |
|---|---|
| Delirium Due to a General Medical Condition | 293.0 |
| Substance-Induced Delirium, including: | |
| Substance Intoxication Delirium: | |
| Code [Specific Substance] Intoxication Delirium: | |
| (291.0 Alcohol; 292.81 Amphetamine [or Amphetamine-Like Substance]; 292.81 Cannabis; 292.81 Cocaine; 292.81 Hallucinogen; 292.81 Inhalant; 292.81 Opioid; 292.81 Phencyclidine [or Phencyclidine-Like Substance]; 292.81 Sedative, Hypnotic, or Anxiolytic; 292.81 Other [or Unknown] Substance [e.g., cimetidine, digitalis, benztropine]) | |
| Substance Withdrawal Delirium: | |
| Code [Specific Substance] Withdrawal Delirium: | |
| (291.0 Alcohol; 292.81 Sedative, Hypnotic, or Anxiolytic; 292.81 Other [or Unknown] Substance) | |
| Delirium Due to Multiple Etiologies: | |
| Multiple codes are used, reflecting the specific delirium and specific etiologies, e.g., 293.0 Delirium Due to Viral Encephalitis; 291.0 Alcohol Withdrawal Delirium | |
| Delirium Not Otherwise Specified | 780.09 |
| Dementia of the Alzheimer's Type | 294.1x* (*ICD-9-CM code) |
| Subtypes: | |
| With Early Onset (onset of the dementia is age 65 years or under) | |
| With Late Onset (onset of the dementia is after age 65 years) | |
| Without Behavioral Disturbance | 294.10 |
| With Behavorial Disturbance | 294.11 |
| Vascular Dementia | 290.4x |
| Subtypes: | |
| With Delirium | 290.41 |
| With Delusions | 290.42 |
| With Depressed Mood | 290.43 |
| With Behavioral Disturbance | Uncoded |
| Uncomplicated | 290.40 |
| Dementia Due to HIV Disease | 294.1x* (*ICD-9-CM code) |
| Dementia Due to Head Trauma | 294.1x* (*ICD-9-CM code) |
| Dementia Due to Parkinson's Disease | 294.1x* (*ICD-9-CM code) |
| Dementia Due to Huntington's Disease | 294.1x* (*ICD-9-CM code) |
| Dementia Due to Pick's Disease | 290.1x* (*ICD-9-CM code) |
| Dementia Due to Creutzfeldt-Jakob Disease | 290.1x* (*ICD-9-CM code) |
| Dementia Due to Other General Medical Conditions | 294.1x* (*ICD-9-CM code) |
| Code based on presence or absence of a clinically significant behavioral disturbance: | |
| Without Behavioral Disturbance | 294.10 |
| With Behavioral Disturbance | 294.11 |
| Substance-Induced Persisting Dementia | |
| Code [Specific Substance]-Induced Persisting Dementia: | |
| (291.2 Alcohol; 292.82 Inhalant; 292.82 Sedative, Hypnotic, or Anxiolytic; 292.82 Other [or Unknown] Substance) | |
| Dementia Due to Multiple Etiologies | |
| Coding note: Use multiple codes based on specific dementias and specific etiologies, e.g., 294.10 Dementia of the Alzheimer's Type, With Late Onset, | |

-continued

| | |
|---|---|
| Without Behavioral Disturbance; 290.40 Vascular Dementia, Uncomplicated. | |
| Dementia Not Otherwise Specified | 294.8 |
| Amnestic Disorder Due to a General Medical Condition Transient or Chronic | 294.0 |
| Substance-Induced Persisting Amnestic Disorder | |
| Code [Specific Substance]-Induced Persisting Amnestic Disorder: 291.1 Alcohol; 292.83 Sedative, Hypnotic, or Anxiolytic; 292.83 Other [or Unknown] Substance | |
| Amnestic Disorder Not Otherwise Specified | 294.8 |
| Cognitive Disorder Not Otherwise Specified | 294.9 |
| Age-Related Cognitive Decline | 780.9 |

Examples of cognitive disorders due to various etiologies, or associated with various disorders, of particular interest that can be prevented or treated using the compounds of the present invention include: enhancing cognitive functions and executive functioning (ability to plan, initiate, organize, carry out, monitor, and correct one's own behavior) in normal subjects or in subjects exhibiting cognitive dysfunction; treatment of cognitive and attentional deficits associated with prenatal exposure to substances of abuse including, but not limited to, nicotine, alcohol, methamphetamine, cocaine, and heroin; treatment of cognitive impairment caused by chronic alcohol and drug abuse (substance-induced persisting dementia), medicament side effects, and treatment of drug craving and withdrawal; treatment of cognitive deficits in Down's Syndrome patients; treatment of deficits in normal memory functioning comorbid with major depressive and bipolar disorders; treatment of cognitive impairment associated with depression, mental retardation, bipolar disorder, or schizophrenia; treatment of dementia syndromes associated with mania, conversion disorder, and malingering; treatment of problems of attention, prefrontal executive function, or memory due to head trauma or stroke; treatment of cognitive dysfunction in menopausal and post-menopausal women and in women undergoing hormone replacement therapy; treatment of cognitive deficits and fatigue due to, or associated with, cancer and cancer therapies (cognitive deficits are associated with a variety of cancer treatments, including cranial radiation, conventional (standard-dose) chemotherapy, high-dose chemotherapy and hematopoietic (bone-marrow) transplantation, and biologic agents).

Compounds which selectively inhibit the reuptake of norepinephrine over serotonin and dopamine are also useful in a method for treating a patient suffering from or susceptible to psychosis, comprising administering to said patient an effective amount of a first component which is an antipsychotic, in combination with an effective amount of a second component which is a compound of formula (I). The invention also provides a pharmaceutical composition which comprises a first component that is an antipsychotic, and a second component that is a compound of formula (I). In the general expressions of this aspect of the present invention, the first component is a compound that acts as an antipsychotic. The antipsychotic may be either a typical antipsychotic or an atypical antipsychotic. Although both typical and atypical antipsychotics are useful for these methods and formulations of the present invention, it is preferred that the first component compound is an atypical antipsychotic.

Typical antipsychotics include, but are not limited to: Chlorpromazine, 2-chloro-10-(3-dimethylaminoprop-yl) phenothiazine, is described in U.S. Pat. No. 2,645,640. Its pharmacology has been reviewed (Crismon, *Psychopharmacol. Bul.* 4, 151 (October 1967); Droperidol, 1-(1-[3-(p-fluorobenzoyl)propyl]-1,2,3,6-tetrahydro-4-pyridyl)-2-benzimidazolinone, is described in U.S. Pat. No. 3,141,823; Haloperidol, 4-[4-(4-chlorophenyl)-4-hydroxy-1-piperidinyl]-1-(4-fluorophenyl)-1-butanone, is described in U.S. Pat. No. 3,438,991. Its therapeutic efficacy in psychosis has been reported (Beresford and Ward, *Drugs,* 33, 31-49 (1987); Thioridazine, 1-hydroxy-10-[2-(1-methyl-2-pyridinyl) ethyl]-2-(methylthio)phenothiazine hydrochloride, was described by Bourquin, et al. (*Helv. Chim. Acta,* 41, 1072 (1958)). Its use as an antipsychotic has been reported (Axelsson, et al., *Curr. Ther. Res.,* 21, 587 (1977)); and Trifluoperazine, 10-[3-(4-methyl-1-piperazinyl)-propyl]-2-trifluoromethylphenthiazine hydrochloride, is described in U.S. Pat. No. 2,921,069.

Atypical antipsychotics include, but are not limited to: Olanzapine, 2-methyl-4-(4-methyl-1-piperazinyl)-10H-thieno[2,3-b][1,5]benzodiazepine, is a known compound and is described in U.S. Pat. No. 5,229,382 as being useful for the treatment of schizophrenia, schizophreniform disorder, acute mania, mild anxiety states, and psychosis; Clozapine, 8-chloro-11-(4-methyl-1-piperazinyl)-5H-dibenzo[b,e][1,4] diazepine, is described in U.S. Pat. No. 3,539,573. Clinical efficacy in the treatment of schizophrenia is described (Hanes, et al., *Psychopharmacol. Bull.,* 24, 62 (1988)); Risperidone, 3-[2-[4-(6-fluoro-1,2-benzisoxazol-3-yl)piperidino]ethyl]-2-methyl-6,7,8,9-tetrahydro-4H-pyrido[1,2-a] pyrimidin-4-one, and its use in the treatment of psychotic diseases are described in U.S. Pat. No. 4,804,663; Sertindole, 1-[2-[4-[5-chloro-1-(4-fluorophenyl)-1H-indol-3-yl]-1-piperidinyl]ethyl]imidazolidin-2-one, is described in U.S. Pat. No. 4,710,500. Its use in the treatment of schizophrenia is described in U.S. Pat. Nos. 5,112,838 and 5,238,945; Quetiapine, 5-[2-(4-dibenzo[b,f][1,4]thiazepin-11-yl-1-piperazinyl)ethoxy]ethanol, and its activity in assays which demonstrate utility in the treatment of schizophrenia are described in U.S. Pat. No. 4,879,288. Quetiapine is typically administered as its (E)-2-butenedioate (2:1) salt; Ziprasidone, 5-[2-[4-(1, 2-benzoisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031; and Aripiprazole (Abilify™), 7-[4-[4-(2,3-dichlorophenyl)-1-piperazinyl]butoxy]-3,4-dihydrocarbostyril (U.S. Pat. Nos. 4,734,416 and 5,006,528) is a new antipsychotic indicated for the treatment of schizophrenia.

It will be understood that while the use of a single antipsychotic as a first component compound is preferred, combinations of two or more antipsychotics may be used as a first component if necessary or desired. Similarly, while the use of a single compound of formula (I) as a second component compound is preferred, combinations of two or more compounds of formula (I) may be used as a second component if necessary or desired.

While all combinations of first and second component compounds are useful and valuable, certain combinations are particularly valued and are preferred, as follows:
 olanzapine/compound of formula (I)
 clozapine/compound of formula (I)
 risperidone/compound of formula (I)
 sertindole/compound of formula (I)
 quetiapine/compound of formula (I)
 ziprasidone/compound of formula (I)
 aripiprazole/compound of formula (I)

In general, combinations and methods of treatment using olanzapine as the first component are preferred. It is especially preferred that when the first component is olanzapine, it will be the Form II olanzapine as described in U.S. Pat. No. 5,736,541. It is further preferred that the Form II olanzapine polymorph will be administered as the substantially pure Form II olanzapine polymorph. As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water. Although Form II olanzapine is preferred it will be understood that as used herein, the term "olanzapine" embraces all solvate and polymorphic forms unless specifically indicated.

Conditions that can be treated by the adjunctive therapy aspect of the present invention include schizophrenia, schizophreniform diseases, bipolar disorder, acute mania, and schizoaffective disorders. The titles given these conditions represent multiple disease states. The following list illustrates a number of these disease states, many of which are classified in the DSM-IV-TR™. The DSM-IV-TR™ code numbers for these disease states are supplied below, when available, for the convenience of the reader.

| | |
|---|---|
| Paranoid Type Schizophrenia | 295.30 |
| Disorganized Type Schizophrenia | 295.10 |
| Catatonic Type Schizophrenia | 295.20 |
| Undifferentiated Type Schizophrenia | 295.90 |
| Residual Type Schizophrenia | 295.60 |
| Schizophreniform Disorder | 295.40 |
| Schizoaffective Disorder | 295.70 |

The present invention also encompasses the use of one or more compounds of formula (I) in combination with one or more conventional Alzheimer's agents for the prevention or treatment of cognitive dysfunction in patients suffering from Alzheimer's disease. The invention also provides a pharmaceutical composition which comprises a first component that is a conventional Alzheimer's agent and a second component that is a compound of formula (I). Conventional Alzheimer's agents include inhibitors of acetylcholine degradation (i.e., cholinesterase or acetylcholinesterase inhibitors) within synapses, e.g., donepezil (Aricept®), rivastigmine (Exelon®), galantamine (Reminyl®), and tacrine (Cognex®); the selective monoamine oxidase inhibitor selegiline (Eldepryl®); and memantine (Namenda™), a newly FDA-approved NMDA receptor antagonist for the treatment of moderate to severe Alzheimer's disease. Modafinil (Provigil®) is also used in the treatment of Alzheimer's disease.

The present invention also encompasses the use of one or more compounds of formula (I) in combination with one or more conventional Parkinson's agents for the treatment of cognitive dysfunction in Parkinson's disease. The invention also provides a pharmaceutical composition which comprises a first component that is a conventional Parkinson's agent and a second component that is a compound of formula (I). Conventional Parkinson's agents include levodopa; levodopa/carbidopa (Sinemet®); Stalevo (carbidopa/levodopa/entacapone); dopamine agonists, e.g., bromocriptine; pergolide; Mirapex® (pramipexole), Permax® (pergolide), and Requip® (ropinirole); COMT inhibitors, e.g., tolcapone, and entacapone; Selegiline (Deprenyl®; Eldepryl®); propranolol; primidone; anticholinergics, e.g., Cogentin®, Artane®, Akineton®, Disipal®, and Kemadrin®; and amantadine.

In each of the combination treatments mentioned above, said first and second components may be administered simultaneously, separately or sequentially. Similarly, said compositions encompass combined preparations for simultaneous, separate or sequential use.

In addition to the compounds of formula (I), and processes for the preparation of said compounds, the present invention further provides pharmaceutical compositions comprising a compound of formula (I), or a pharmaceutically acceptable salt thereof, together with a pharmaceutically acceptable diluent, excipient or carrier.

The compounds of the present invention may be used as medicaments in human or veterinary medicine. The compounds may be administered by various routes, for example, by oral or rectal routes, topically or parenterally, for example by injection, and are usually employed in the form of a pharmaceutical composition. Such compositions may be prepared by methods well known in the pharmaceutical art and normally comprise at least one active compound in association with a pharmaceutically acceptable diluent, or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosols (as a solid or in a liquid medium), ointments containing, for example, up to 10% by weight of the active compound, soft and hard gelatin capsules, suppositories, injection solutions and suspensions and sterile packaged powders. Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propyl-hydrobenzoate, talc, magnesium stearate and mineral oil. The compounds of formula (I), can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a dosage unit form each dosage unit containing from about 5 to about 500 mg, more usually about 25 to about 300 mg, of the active ingredient. The term "dosage unit form" refers to physically discrete units, such as tablets or capsules, suitable as unitary doses for human subjects and other mammals, each unit containing a predetermined quantity of active material calculated to produce the desired therapeutic effect, in association with a suitable pharmaceutical carrier.

The following examples illustrate particular embodiments of compounds of the present invention and methods for their preparation.

Preparation of Intermediates (2S)-(4-Benzyl-morpholin-2-yl)-phenyl-methanone (1)

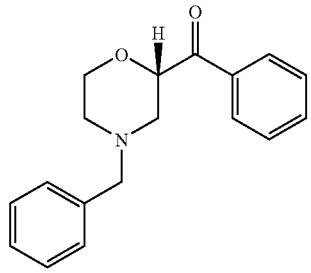

A 1600 L GL reactor under $N_2$ is successively loaded with 2-chloroacrylonitrile (33.2 kg, 379 moles) and toluene (114 L) at 21° C. Then, N-benzylethanolamine (57 kg, 377 moles) is added and the reaction mixture is post-agitated at room temperature for about 17 h. Then, the mixture is diluted with toluene (336 L), cooled down to −12.4° C. and potassium t-butoxide (42.3 kg, 377 moles) is added in portions (10) maintaining −13.7° C.≦Tmass≦−2.8° C. The mixture is post-agitated at about 0° C. for 2.5 h, and quenched by adding ultra pure water (142.5 L) maintaining 2.1° C.≦Tmass≦8.7° C. The aqueous layer (176 kg) is separated after 35 minutes of post-stirring allowing the mixture to reach 15° C. and the toluene layer is washed with ultra pure water (142.5 L) and the aqueous layer (162 kg) is separated. The organic layer is then concentrated under reduced pressure (150 mbars) maintaining Tmass≦60° C. in order to distill 162 kg of toluene. The filtrates are then diluted with toluene (114 L) and treated with $SiO_2$ (Merck silica gel 60, 0.063-0.1 mm, 74.1 kg) under agitation at room temperature for 1.25 h. $SiO_2$ is filtered and rinsed with toluene (2×114 L). Then, the filtrates are concentrated under reduced pressure (150 mbars) maintaining Tmass≦60° C. in order to distill 351.8 kg of toluene (KF: 0.01% w/w $H_2O$).

The solution of 4-benzyl-morpholine-2-carbonitrile (169.2 kg) is diluted with toluene (157 L) and is cooled to 0° C. and phenylmagnesiumchloride (25 wt. % solution in THF, 213 kg, 389 moles, 1.36 molar equiv.) is slowly added (over 3.5 h) to the reaction mixture, maintaining the temperature at −3° C.≦Tmass≦7° C. The reaction mixture is post-stirred for 2 hours at Tmass~0° C. Then, the quench is performed by adding acetic acid (8.55 L, Tmass=5→17.2° C.), post stirring 10 minutes and cooling to 5° C. before adding an acetic acid/water mixture (229 L, 33/67 v/v). During the quench, addition is performed at such a rate that Tmass does not exceed 20° C. (typical Tmass=4.6° C. to 10.4° C.). The mixture is post-agitated overnight at RT and the aqueous layer (285.8 kg) is extracted.

The toluene layer is cooled to 0° C. and a 5 N NaOH aqueous solution (420.1 kg) is slowly added maintaining the temperature at −2.4° C.≦Tmass≦11° C. The reaction mixture is post-stirred for 1 h and the aqueous layer (494.8 kg) is extracted. The toluene layer is concentrated under reduced pressure (50 mbars) maintaining Tmass≦60° C. in order to distill 356.2 kg of toluene and isopropanol (180.4 kg) is added. The toluene is stripped off under reduced pressure (100 mbars) maintaining Tmass≦60° C. in order to distill 186.4 kg of toluene and isopropanol (135 kg) is added again to the mixture. A last distillation of toluene is performed under reduced pressure (50 mbars) maintaining Tmass≦60° C. in order to distill 131 kg of toluene and isopropanol (49.4 kg) is finally added to the mixture and the solution is stirred at RT until crystallization (17 minutes).

Ultra pure water is added (125.4 L) and the mixture is stirred overnight at RT and cooled down to about 0° C. for 1 hour. The precipitate is filtered and rinsed with a cooled water/isopropanol 50/50 v/v solution (76.6 kg). The wet precipitate is dried under vacuum at Tjack=35° C. for 96 hours to obtain the title compound as an off-white powder with 59% overall yield. The title compound may be resolved by fractional crystallisation from acetonitrile using from 0.55 to 1 equivalent of dibenzoyltartaric acid to generate diastereoisomeric salts of the title compound. The crystals may be collected by filtration and neutralized with 30% NaOH to afford the optically enriched title compound.

(S)-Phenyl[(2S)-4-(phenylmethyl)morpholin-2-yl] methanol (2)

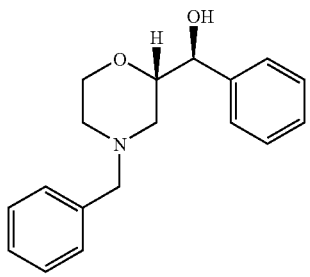

To a stirred solution of [(−)-B-chlorodiisopinocampheylborane] (45 g, 140 mmol) in dry tetrahydrofuran (300 ml) under nitrogen is added (2S)-(4-Benzyl-morpholin-2-yl)-phenyl-methanone (1) (7.97 g, 28.4 mmol) in one portion. The reaction mixture is stirred at room temperature for 18 hours. The mixture is evaporated in vacuo and extracted from 2M aqueous sodium hydroxide solution into ethyl acetate. The combined organic extracts are washed with brine, dried, filtered and evaporated. The crude product is taken up in chloroform/methanol (1:1 [v/v]) and absorbed onto 150 g SCX-2 ion exchange resin. After elution of borane residues with methanol the product is eluted with 2M ammonia in methanol. Removal of solvent in vacuo yielded the product as a yellow oil. This is further purified by flash chromatography (eluent:ethyl acetate/isohexane 80/20 [v/v]). After removal of solvents, the product crystallised on standing (6.73 g, 84%); MW 283.37; $C_{18}H_{21}NO_2$; $^1H$ NMR (CDCl$_3$): 7.32-7.45 (10H, m), 4.67 (1H, d, 7 Hz), 4.03 (1H, dt, 11 Hz and 2 Hz), 3.86-3.73 (2H, m), 3.64 (1H, d, 13 Hz), 3.39 (1H, d, 13 Hz), 3.30 (1H, br, s), 2.68 (1H, d, 12 Hz), 2.56 (1H, d, 10 Hz), 2.28-2.15 (2H, m); LCMS: m/z 284 [M+H]+@ Rt 0.95 min.

(2S)-2-[(R)-bromo(phenyl)methyl]-4-(phenylmethyl) morpholine (3)

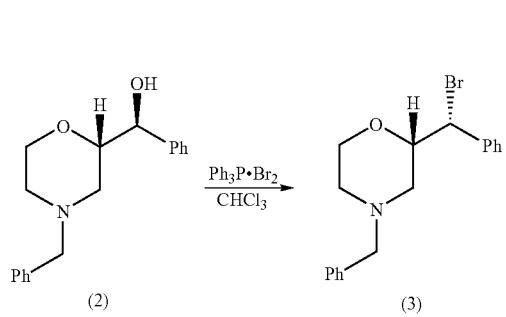

To a solution of (S)-phenyl[(2S)-4-(phenylmethyl)morpholin-2-yl]methanol (2) (4.71 g, 16.63 mmole) in chloroform (200 ml) is added the triphenylphosphine dibromide (14.04 g, 33.26 mmole). The mixture is heated at 60° C. overnight. The mixture is allowed to cool to room temperature then washed with saturated sodium carbonate solution (aqueous, ~100 ml), dried (Na$_2$SO$_4$) and concentrated in vacuo. The resulting residue is purified by automated flash chromatography (ISCO system: 120 g column, 10-30% EtOAc in isohexane) to give (2S)-2-[(R)-bromo(phenyl)methyl]-4-(phenylmethyl)morpholine (3) as a white solid (4.63 g, 80%). LCMS 6 min gradient method, Rt=2.5 min, (M+H$^+$)=346/348

S-{(S)-phenyl[(2S)-4-(phenylmethyl)morpholin-2-yl]methyl}ethanethioate (5)

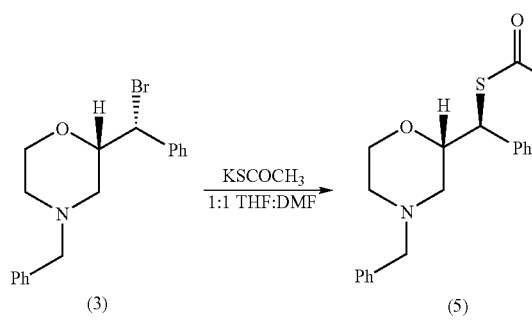

A solution of (2S)-2-[(R)-bromo(phenyl)methyl]-4-(phenylmethyl)morpholine (3) (1.76 g, 5.08 mmole) and potassium thiolacetate (1.16 g, 10.16 mmole) in 1:1 anhydrous THF:DMF (30 ml), is stirred at 40° C. under nitrogen overnight. The mixture is then taken up in acetonitrile and loaded onto an SC10-2 column (4×10 g). The SC10-2 columns are washed with further acetonitrile. The target compound is eluted with 4:1 acetonitrile:Et$_3$N. This is concentrated in vacuo to give an orange oil which is purified by automated flash chromatography (ISCO system: 35 g SiO$_2$ Redisep column, 10-30% EtOAc in isohexane over 40 minutes) to give S-{(S)-phenyl[(2S)-4-(phenylmethyl)morpholin-2-yl] methyl}ethanethioate (5) as an amber coloured crystalline solid (1.54 g, 89%). LCMS 6 min gradient method, Rt=2.5 min, (M+H$^+$)=342

(S)-phenyl[(2S)-4-(phenylmethyl)morpholin-2-yl] methanethiol (6)

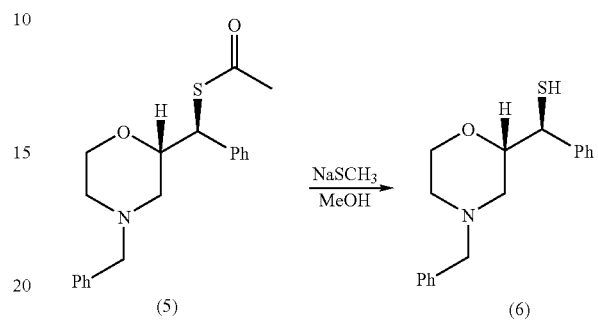

The S-{(S)-phenyl[(2S)-4-(phenylmethyl)morpholin-2-yl]methyl}ethanethioate (5) (11.02 g, 32.3 mmole) is taken up in methanol (100 ml, dry, degassed), under nitrogen. To this is added the sodium thiomethoxide (2.26 g, 32.3 mmole) in one portion (as solid). The reaction mixture is left to stir at room temperature for 2 hours. The solution is then added to an aqueous solution of HCl (0.1 M). This is extracted with DCM (3×). The extracts are dried (Na$_2$SO$_4$) and concentrated in vacuo to give (S)-phenyl[(2S)-4-(phenylmethyl)morpholin-2-yl]methanethiol (6) as a yellow solid (9.59 g, 99%). LCMS 6 min gradient method, Rt=2.7 min, (M+H$^+$)=300

EXAMPLES

Example 1

(2S)-2-{(S)-phenyl[(3-phenylpyridin-2-yl)thio] methyl}morpholine hemifumarate

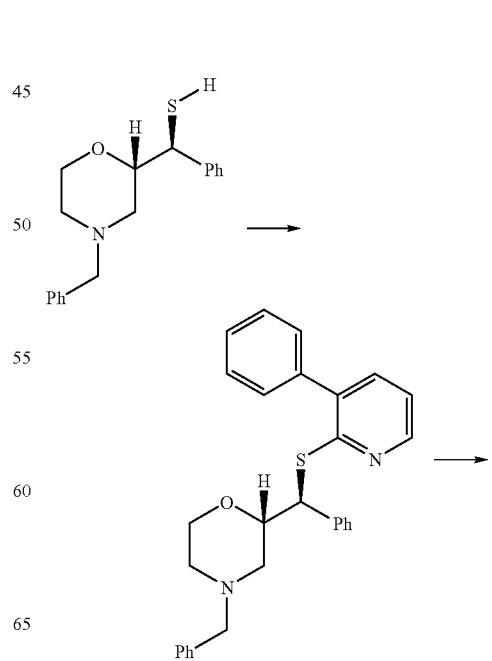

-continued

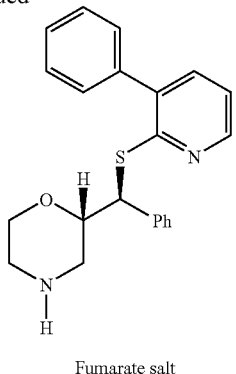

Fumarate salt i) To palladium acetate (0.026 g, 0.12 mmole) in acetonitrile (3 ml), is added triphenylphosphine (0.122 g, 0.46 mmole), under nitrogen, at room temperature. The mixture is left to stir for 15 minutes. To this mixture is added water (distilled, 1 ml), phenylboronic acid (0.846 g, 6.94 mmole), 3-bromo-2-fluoropyridine (1.02 g, 5.78 mmole) and potassium carbonate (4.80 g, 34.70 mmole). The reaction mixture is heated at 70° C. overnight. After cooling to room temperature, the reaction mixture is loaded directly onto a 40 g Redisep SiO$_2$ column and components isolated by automated flash chromatography (ISCO System, 0-30% ethyl acetate in cyclohexane gradient elution over 40 minutes). This gave 2-fluoro-3-phenylpyridine as a very pale yellow oil (1.00 g, 100%). LCMS 6 min gradient method, Rt=3.7 min, (M+H$^+$)=174.

ii) To a solution of (S)-phenyl[(2S)-4-(phenylmethyl)morpholin-2-yl]methanethiol (6) (1.50 g, 5.01 mmole) and 2-fluoro-3-phenylpyridine (2.44 g, 14.09 mmole) in dry, degassed DMF (10 ml) is added, under nitrogen, sodium hydride (60% dispersion in oil, 0.24 g, 6.01 mmole). The mixture is left to stir overnight at room temperature. The reaction mixture is loaded neat onto a 120 g SiO$_2$ Redisep column (preconditioned with cyclohexane). Automated flash chromatography (ISCO System, 0-30% ethyl acetate in cyclohexane gradient elution over 40 minutes at 40 ml/minute flow rate) yielded an orange oil (2.26 g). Chromatography is repeated using chromatography (ISCO System, 40 g column, 0-30% ethyl acetate in cyclohexane gradient elution over 40 minutes at 30 ml/minute flow rate) to give (2S)-2-{(S)-phenyl[(3-phenylpyridin-2-yl)thio]methyl}-4-(phenylmethyl)morpholine as a pale orange oil (1.65 g, 73%). LCMS 6 min gradient method, Rt=4.0 min, (M+H$^+$)=453.

iii) To a suspension of polymer supported diisopropylamine (3.78 mmol/g, 0.54 g, 2.03 mmole) and (2S)-2-{(S)-phenyl[(3-phenylpyridin-2-yl)thio]methyl}-4-(phenylmethyl)morpholine (0.184 g, 0.41 mmole) in dry DCM (5 ml) is added 1-chloroethyl chloroformate (0.22 ml, 2.03 mmole) at room temperature and under nitrogen. The mixture is heated at 40° C. for 3.75 hours. The reaction mixture is filtered, concentrated in vacuo then taken up in methanol (5 ml). The solution is left to stir at room temperature overnight. After this time, the reaction mixture is loaded directly onto an SC10-2 column. The SC10-2 column is washed with methanol. The title compound is eluted with 2 N NH$_3$/methanol. This is concentrated in vacuo to give (2S)-2-{(S)-phenyl[(3-phenylpyridin-2-yl)thio]methyl}morpholine as white foam (0.148 g, 100%). The foam is taken up in ethyl acetate. To this is added a solution of fumaric acid (1.1 equiv, 0.052 g) in methanol. The resulting solution is filtered then concentrated in vacuo. To the resulting white solid is added methanol (1.5 ml). This is stirred for a couple of minutes, then the remaining solid collected by filtration to give the hemi-fumarate salt of (2S)-2-{(S)-phenyl[(3-phenylpyridin-2-yl)thio]methyl}morpholine as a white solid (0.127 g). LCMS 12 min gradient method, Rt=5.5 min, (M+H$^+$)=363

Example 2

(2S)-2-[(S)-{[3-(4-fluorophenyl)pyridin-2-yl]thio}(phenyl)methyl]morpholine fumarate

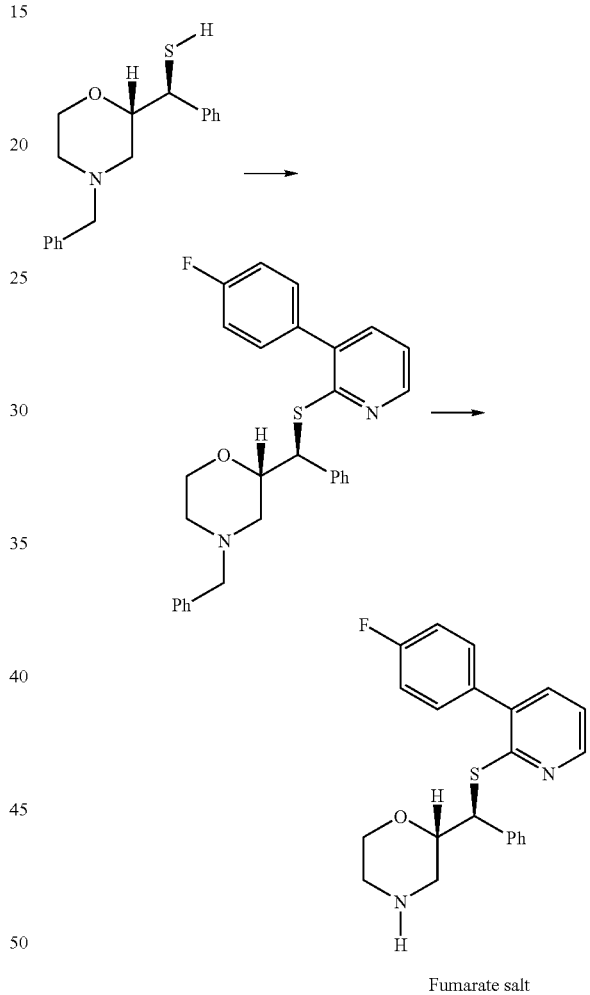

Fumarate salt i) To bis(benzonitrile)palladium(II)dichloride (0.054 g, 0.14 mmole) and 1,4-bis(diphenylphosphine)butane (0.091 g, 0.21 mmole) is added dry toluene (6 ml), under nitrogen, and the mixture stirred for half an hour. To this is added 3-bromo-2-fluoropyridine (0.50 g, 2.83 mmole) in ethanol (1.4 ml) followed by a solution of 4-fluorophenylboronic acid (0.793 g, 5.67 mmole) in ethanol (2.4 ml). To this is added an aqueous solution of sodium carbonate (1 M, 2.83 ml, 2.83 mmole). The mixture is heated at 60° C. for 24 hours, then at 75° C. for a further 16 hours. The organic layer is loaded directly onto a 40 g Redisep SiO$_2$ column and components isolated by automated flash chromatography (ISCO System, 0-30% ethyl acetate in cyclohexane gradient elution over 40 minutes). This gave 3-(4-fluorophenyl)-2-fluoropyridine as a white solid (0.387 g, 71%). LCMS 6 min gradient method, Rt=3.6 min, (M+H$^+$)=192 ii) To a solution of (S)-phenyl[(2S)-4-(phenylmethyl)morpholin-2-yl]methanethiol (6) (0.505 g, 1.69 mmole) and 3-(4-fluorophenyl)-2-fluoropyridine (0.387 g, 2.02 mmole) in dry, degassed DMF (3 ml) is added, under nitrogen, cesium fluoride (0.385 g, 2.54 mmole). The mixture is heated at 65° C. over the weekend. After this time, the reaction mixture is allowed to cool and loaded directly onto an SC10-2 column. The SC10-2 column is washed with methanol. The (2S)-2-[(S)-{[3-(4-fluorophenyl)pyridin-2-yl]thio}(phenyl)methyl]-4-(phenylmethyl)morpholine is eluted with 2 N NH$_3$/methanol. This is concentrated in vacuo to give an orange solid (0.649 g). This is purified by automated flash chromatography (ISCO System, 40 g SiO$_2$ Redisep column, 0-30% ethyl acetate in cyclohexane gradient elution over 40 minutes at 30 ml/minute flow rate) to give (2S)-2-[(S)-{[3-(4-fluorophenyl)pyridin-2-yl]thio}(phenyl)methyl]-4-(phenylmethyl)morpholine as a off-white foam (0.395 g, 50%). LCMS 6 min gradient method, Rt=3.3 min, (M+H$^+$)=471.

iii) Deprotection of the morpholine nitrogen is carried out using the method and work up as described in Example 1, using polymer supported diisopropylamine (3.78 mmole/g, 1.09 g, 4.14 mmole), (2S)-2-[(S)-{[3-(4-fluorophenyl)pyridin-2-yl]thio}(phenyl)methyl]-4-(phenylmethyl)morpholine (0.390 g, 0.83 mmole), dry DCM (20 ml), 1-chloroethyl chloroformate (0.45 ml, 4.14 mmole) and methanol (20 ml). This gave (2S)-2-[(S)-{[3-(4-fluorophenyl)pyridin-2-yl]thio}(phenyl)methyl]morpholine as a pale yellow oil (0.232 g, 74%). This oil is taken up in ethyl acetate. To this is added a solution of fumaric acid (1.1 equiv, 0.071 g) in methanol. The resulting solid is collected by filtration to give a white solid (0.115 g). This is recrystallised from MeOH/CHCl$_3$/Et$_2$O to give a white solid (0.061 g). LCMS 12 min gradient method, Rt=5.4 min, (M+H$^+$)=381

Example 3

(2S)-2-[(S)-{[3-(3-chlorophenyl)pyridin-2-yl]thio{(phenyl)methyl]morpholine fumarate

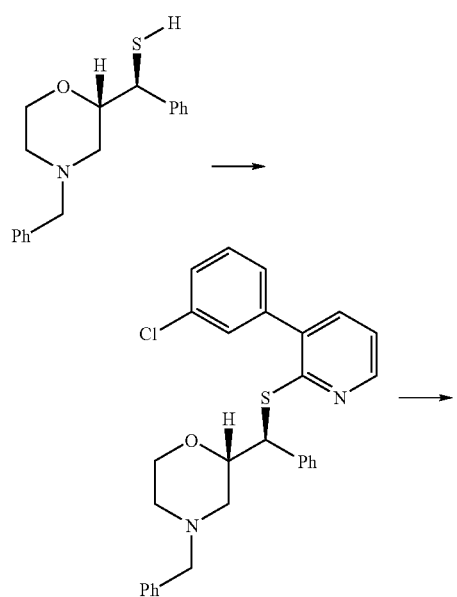

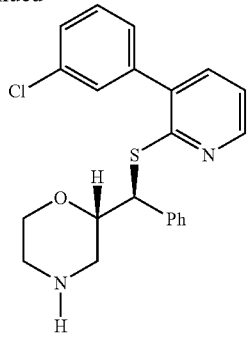

Fumarate salt i) To bis(benzonitrile)palladium(II)dichloride (0.054 g, 0.14 mmole) and 1,4-bis(diphenylphosphine)butane (0.091 g, 0.21 mmole) is added dry toluene (6 ml), under nitrogen, and the mixture stirred for half an hour. To this is added 3-bromo-2-fluoropyridine (0.50 g, 2.83 mmole) in ethanol (1.4 ml) followed by a solution of 3-chlorophenylboronic acid (0.887 g, 5.67 mmole) in ethanol (2.4 ml). To this is added an aqueous solution of sodium carbonate (1 M, 2.83 ml, 2.83 mmole). The mixture is heated at 60° C. for 24 hours, then at 75° C. for a further 16 hours. The organic layer is loaded directly onto a 40 g Redisep SiO$_2$ column and components isolated by automated flash chromatography (ISCO System, 0-30% ethyl acetate in cyclohexane gradient elution over 40 minutes). This gave 3-(3-chlorophenyl)-2-fluoropyridine as an off-white solid (0.333 g, 57%). LCMS 6 min gradient method, Rt=4.0 min, (M+H$^+$)=208.

ii) To a solution of (S)-phenyl[(2S)-4-(phenylmethyl)morpholin-2-yl]methanethiol (6) (0.400 g, 1.34 mmole) and 3-(3-chlorophenyl)-2-fluoropyridine (0.333 g, 1.60 mmole) in dry, degassed DMF (3 ml) is added, under nitrogen, cesium fluoride (0.305 g, 2.00 mmole). The mixture is heated at 65° C. over the weekend. After this time, the reaction mixture allowed to cool. The resulting solid is taken up in MeOH/DCM and loaded directly onto an SC10-2 column. The SC10-2 column is washed with methanol. The (2S)-2-[(S)-{[3-(3-chlorophenyl)pyridin-2-yl]thio}(phenyl)methyl]-4-(phenylmethyl)morpholine is eluted with 2 N NH$_3$/methanol. This is concentrated in vacuo to give a white foam (0.555 g). This is purified by automated flash chromatography (ISCO System, 0-30% ethyl acetate in cyclohexane gradient elution over 40 minutes at 40 ml/minute flow rate) to yield (2S)-2-[(S)-{[3-(3-chlorophenyl)pyridin-2-yl]thio}(phenyl)methyl]-4-(phenylmethyl)morpholine as a white foam (0.258 g, 40%). LCMS 6 min gradient method, Rt=4.2 min, (M+H$^+$)=487.

iii) Deprotection of the morpholine nitrogen is carried out using the method and work up as described in Example 1, using polymer supported diisopropylamine (3.72 mmole/g, 0.70 g, 1.80 mmole), (2S)-2-[(S)-{[3-(3-chlorophenyl)pyridin-2-yl]thio}(phenyl)methyl]-4-(phenylmethyl)morpholine (0.255 g, 0.52 mmole), dry DCM (15 ml), 1-chloroethyl chloroformate (0.29 ml, 2.62 mmole) and methanol (15 ml). This gave a colourless residue (0.211 g). This residue is taken up in ethyl acetate. To this is added a solution of fumaric acid (1.1 equiv, 0.062 g) in methanol. If the resulting solid contains impurities it may be recombined with the mother liquor and purified on a UV Guided PrepHPLC (Flex) System and treated with SC10-2 to give (2S)-2-[(S)-{[3-(3-chlorophenyl)pyridin-2-yl]thio}(phenyl)methyl]morpholine as a pale yellow oil (0.127 g, 65%). This oil is taken up in MeOH/DCM. To this is added a solution of fumaric acid (1.1 equiv, 0.0145 g) in methanol, followed by Et$_2$O. The resulting crystals are collected by filtration to give the fumarate salt of (2S)-2-[(S)-{[3-(3-chlorophenyl)pyridin-2-yl]thio}(phenyl)methyl]morpholine (1:1 fumarate salt) as a white solid (0.047 g). LCMS 12 min gradient method, Rt=5.7 min, (M+H$^+$)=397

Example 4

(2S)-2-[{[3-(2-chlorophenyl)pyridin-2-yl]thio}(phenyl)methyl]morpholine fumarate

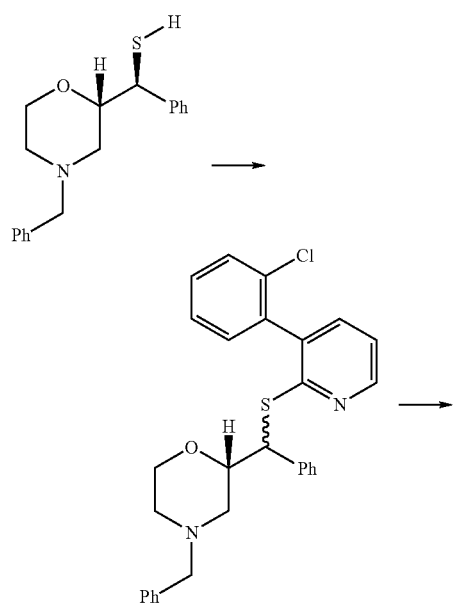

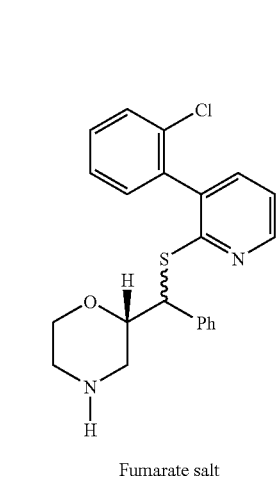

Fumarate salt i) To palladium acetate (0.0025 g, 0.0011 mmole) in acetonitrile (3 ml), is added triphenylphosphine (0.0119 g, 0.045 mmole), under nitrogen, at room temperature. The mixture is left to stir for 15 minutes. To this mixture is added water (distilled, 1 ml), 2-chlorophenylboronic acid (0.106 g, 0.68 mmole), 3-bromo-2-fluoropyridine (0.10 g, 0.57 mmole) and potassium carbonate (0.470 g, 3.40 mmole). The reaction mixture is heated to 60° C. increasing to 75° C. over 5 hours then allowed to cool to room temperature. To the reaction mixture is added MeOH and this is loaded onto an SC10-2 column (10 g) preconditioned with MeOH. The column is washed with MeOH and the resulting solution concentrated in vacuo to give an orange oil (0.196 g). The oil is purified by automated flash chromatography (ISCO System, a 10 g Redisep SiO$_2$ column, 0-30% ethyl acetate in cyclohexane gradient elution over 40 minutes). This gave 2-fluoro-3-(2-chlorophenyl)pyridine as a colourless oil (0.050 g, 42%). LCMS 6 min gradient method, Rt=3.3 min, (M+H$^+$)=208 ii) To a solution of (S)-phenyl[(2S)-4-(phenylmethyl)morpholin-2-yl]methanethiol (6) (0.288 g, 0.96 mmole) and 3-(2-chlorophenyl)-2-fluoropyridine (0.40 g, 1.93 mmole) in dry, degassed DMF (2 ml) is added, under nitrogen, sodium hydride (60% dispersion in oil, 0.0.046 g, 1.15 mmole). The mixture is left to stir at room temperature over the weekend. The reaction mixture is loaded directly onto an a 40 g Redisep SiO$_2$ column. Components are eluted using automated flash chromatography (ISCO System, 0-30% ethyl acetate in cyclohexane gradient elution over 30 minutes at 40 ml/minute flow rate) to give (2S)-2-[{[3-(2-chlorophenyl)pyridin-2-yl]thio}(phenyl)methyl]-4-(phenylmethyl)morpholine as a white solid (0.021 g, 5%). LCMS 6 min gradient method, Rt=4.3 min, (M+H$^+$)=487.

iii) Deprotection of the morpholine nitrogen is carried out using the method and work up as described in Example 1, using polymer supported diisopropylamine (3.78 mmole/g, 0.057 g, 0.216 mmole), (2S)-2-[{[3-(2-chlorophenyl)pyridin-2-yl]thio}(phenyl)methyl]-4-(phenylmethyl)morpholine (0.021 g, 0.043 mmole), dry DCM (2 ml), 1-chloroethyl chloroformate (0.024 ml, 0.216 mmole) and methanol (2 ml). This gave a colourless residue (0.017 g, 100%). This residue is taken up in ethyl acetate. To this is added a solution of fumaric acid (1 equiv, 0.005 g) in methanol. This is reduced in volume and Et$_2$O added. The resulting solid is collected by filtration to give the fumarate salt of (2S)-2-[{[3-(2-chlorophenyl)pyridin-2-yl]thio}(phenyl)methyl]morpholine (1:1 fumarate salt) as a pale green solid (0.012 g). LCMS 12 min gradient method, Rt=5.4 min, (M+H$^+$)=397

Example 5

(2S)-2-((S)-phenyl{[3-(trifluoromethyl)pyridin-2-yl]thio}methyl)morpholine

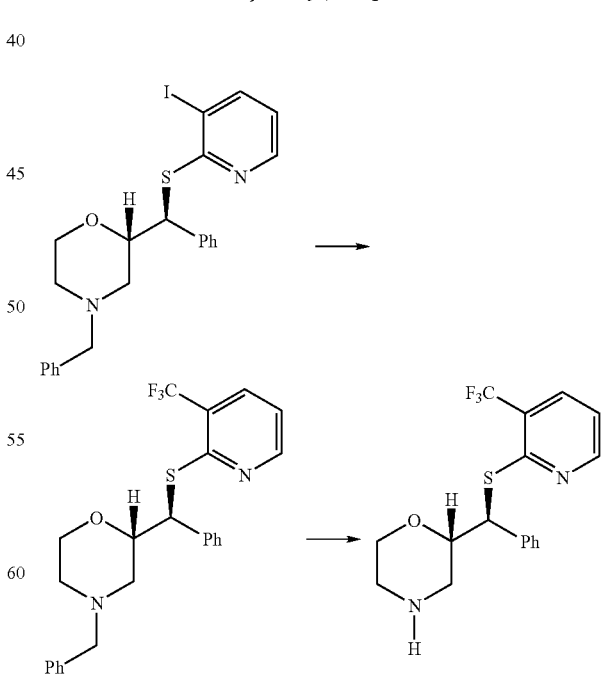

i) Potassium fluoride (0.048 g, 0.84 mmole) and copper (I) iodide (0.159 g, 0.84 mmole) are thoroughly mixed and dried under reduced pressure with a hot air gun for 20 minutes. To the resulting yellow solid, at room temperature is added (2S)-2-[(S)-[(3-iodopyridin-2-yl)thio](phenyl)methyl]-4-(phenylmethyl)morpholine (as prepared in Example 15) (0.190 g, 0.38 mmole) in anhydrous NMP (0.5 ml) followed by anhydrous DMF (0.5 ml) then (trifluoromethyl)trimethylsilane (0.11 ml, 0.76 mmole). After 3 days at room temperature, the temperature is increased to 50° C. The reaction mixture is heated at 50° C. overnight. After cooling to room temperature, further (trifluoromethyl)trimethylsilane (0.11 ml, 0.76 mmole) is added to the reaction mixture and the mixture is left to stir overnight at room temperature. To the reaction mixture is added MeOH before loading onto an SC10-2 column (10 g) preconditioned with MeOH. The column is washed with MeOH. Basic material is eluted with 2 N NH$_3$/methanol. This is concentrated in vacuo to give a pale yellow solid (0.199 g). This is purified by automated flash chromatography (ISCO System, 3×4 g Redisep SiO$_2$ columns, in parallel, 0-20% ethyl acetate in cyclohexane gradient elution over 40 minutes) to give the (2S)-2-[(S)-[(3-iodopyridin-2-yl)thio](phenyl)methyl]-4-(phenylmethyl)morpholine as a white foam (0.108 g, 57% recovery of this starting material) and (2S)-2-((S)-phenyl{[3-(trifluoromethyl)pyridin-2-yl]thio}methyl)-4-(phenylmethyl)morpholine as a colourless oil (0.033 g, 20%). LCMS 6 min gradient method, Rt=4.2 min, (M+H$^+$)=445 ii) To a suspension of polymer supported diisopropylamine (3.72 mmol/g, 0.097 g, 0.36 mmole) and (2S)-2-((S)-phenyl{[3-(trifluoromethyl)pyridin-2-yl]thio}methyl)-4-(phenylmethyl)morpholine (0.0.032 g, 0.07 mmole) in dry DCM (0.5 ml) is added 1-chloroethyl chloroformate (0.039 ml, 0.36 mmole) at room temperature and under nitrogen. The mixture is heated at 40° C. for 2 hours. The reaction mixture is filtered and concentrated in vacuo then taken up in methanol (0.5 ml). The solution left to stir at room temperature overnight. After this time, the reaction mixture is loaded directly onto an SC10-2 column. The SC 10-2 column is washed with methanol. The target compound is eluted with 2 N NH$_3$/methanol. This is concentrated in vacuo to give a pale yellow oil (0.024 g). The pale yellow oil is purified using an automated PrepLCMS system, then liberated as the free base by treatment with SC10-2 and concentrated under vacuum to give (2S)-2-((S)-phenyl{[3-(trifluoromethyl)pyridin-2-yl]thio}methyl)morpholine as a white solid (0.005 g, 20%). LCMS 12 min gradient method, Rt=4.9 min, (M+H$^+$)=354

Example 6

(2S)-2-((S)-phenyl{[3-(phenylmethyl)pyridin-2-yl]thio{methyl)morpholine fumarate

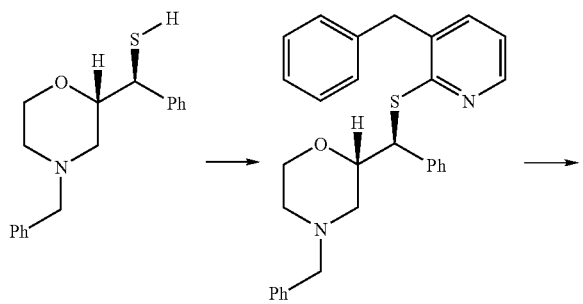

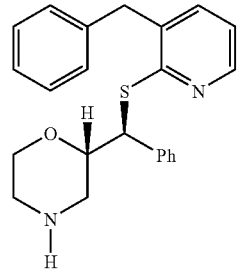

Fumarate salt i) To a 100 ml round-bottomed flask, under nitrogen, containing dry THF (25 ml) is added n-butyllithium (1.6 M solution in hexanes, 3.99 ml, 6.39 mmole) at 0° C. followed by lithium diisopropylamide (2 M solution in THF/n-heptane, 3.19 ml, 6.39 mmole). The reaction mixture is left to stir for 1 hour at 0° C. The mixture is cooled to −70° C. then 2-fluoropyridine added. The solution is stirred at −70° C. for 4 hours. To the solution is added benzaldehyde (0.71 ml, 6.97 mmole). This is then left to stir for 1 hour at −70° C., after which time water (100 ml) is added. On warming to room temperature the solution is extracted with chloroform (2×100 ml). The combined extracts are dried (Na$_2$SO$_4$) and concentrated in vacuo to yield a yellow oil (1.58 g). Purification by automated flash chromatography (ISCO System, Redisep 10 g SiO$_2$ column, 0-30% ethyl acetate in cyclohexane gradient elution over 30 minutes at 20 ml/min flow rate) gave 2-fluoro-3-(phenyl-1-hydroxymethyl)pyridine as a yellow oil (0.71 g, 59%). FIA (M+H$^+$)=204 ii) To 5% Pd/C (0.07 g), under nitrogen, is added a solution of 2-fluoro-3-(1-hydroxy-1-phenylmethyl)pyridine (0.71 g, 3.5 mmole) in ethanol (50 ml). This is then put on a Parr Hydrogenator at 60 psi H$_2$ and left over the weekend. The reaction mixture is filtered through Celite®. Removal of solvent from the resulting solution gave a pale yellow oil. This is purified by automated flash chromatography (ISCO System, 10 g SiO$_2$ Redisep column, 0-30% ethyl acetate in cyclohexane gradient elution over 40 minutes at 20 ml/minute flow rate) to give 2-fluoro-3-(phenylmethyl)pyridine as a colourless oil (0.18 g, 27%).

iii) To a solution of (S)-phenyl[(2S)-4-(phenylmethyl)morpholin-2-yl]methanethiol (6) (0.27 g, 0.91 mmole) and 2-fluoro-3-(1-hydroxy-1-phenylmethyl)pyridine (0.17 g, 0.91 mmole) in dry, degassed DMF (1.5 ml) is added, under nitrogen, sodium hydride (60% dispersion in oil, 0.07 g, 1.82 mmole). The mixture is left to stir overnight at room temperature. A further portion of sodium hydride (605 dispersion in oil, 0.07 g, 1.82 mmole) and DMF (1 ml) is added. After 5 hours at room temperature, the reaction mixture is taken up in MeOH and loaded onto an SC10-2 column. The SC10-2 column is washed with methanol. The (2S)-2-((S)-phenyl{[3-(phenylmethyl)pyridin-2-yl]thio}methyl)-4-(phenylmethyl) morpholine is eluted with 2 N NH$_3$/methanol. This is concentrated in vacuo to give a yellow residue (0.36 g). The residue is purified by automated flash chromatography (ISCO System, 35 g SiO$_2$ Redisep column, 0-30% ethyl acetate in cyclohexane gradient elution over 40 minutes at 40 ml/minute flow rate) which yields (2S)-2-((S)-phenyl{[3-(phenylmethyl)pyridin-2-yl]thio}methyl)-4-(phenylmethyl)morpholine as a pale yellow oil (0.10 g, 24%). LCMS 6 min gradient method, Rt=3.8 min, (M+H$^+$)=467 iv) Deprotection of the morpholine nitrogen is carried out using the method and work up as described in Example 1, using polymer supported diisopropylamine (3.78 mmole/g, 0.28 g, 1.07 mmole), of (2S)-2-((S)-phenyl{[3-(phenylmethyl)pyridin-2-yl]thio}methyl)-4-(phenylmethyl)morpholine (0.092 g, 0.20 mmole), dry DCM (5 ml), 1-chloroethyl chloroformate (0.12 ml, 1.07 mmole) and methanol (5 ml). This gives (2S)-2-((S)-phenyl{[3-(phenylmethyl)pyridin-2-yl]thio}methyl)morpholine as a colourless residue (0.076 g, 94%). This oil is taken up in ethyl acetate. To this is added a solution of fumaric acid (1.1 equiv, 0.026 g) in methanol. The resulting solution is concentrated in vacuo and the resulting oil triturated with ethyl acetate. The solid is collected by filtration to give the fumarate salt of (2S)-2-((S)-phenyl{[3-(phenylmethyl)pyridin-2-yl]thio}methyl)morpholine (1:1 fumarate salt) as a white solid (0.070 g). LCMS 12 min gradient method, Rt=5.6 min, (M+H$^+$)=377

Example 7

(2S)-2-((S)-phenyl{[3-(phenyloxy)pyridin-2-yl]thio}methyl)morpholine fumarate

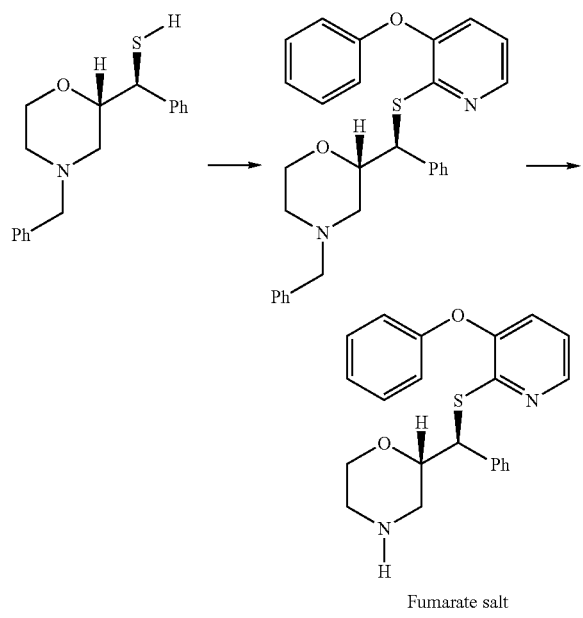

Fumarate salt i) To a 100 ml round bottomed flask is added 2-chloro-3-pyridinol (0.50 g, 3.86 mmole), copper (II) acetate (0.70 g, 3.86 mmole), phenylboronic acid (0.94 g, 7.72 mmole) and powdered 4 Å molecular sieves. To the mixture is added DCM (39 ml) followed by triethylamine (2.69 ml, 19.30 mmole). This is stirred overnight, under nitrogen, at room temperature. The reaction mixture is poured into water (75 ml) and extracted with ethyl acetate (3×75 ml). The combined extracts are concentrated in vacuo to give a brown oil (0.65 g). Purification by automated flash chromatography (ISCO System, Redisep 35 g SiO$_2$ column, 0-20% ethyl acetate in cyclohexane gradient elution over 40 minutes) gives 2-chloro-3-phenoxypyridine as a colourless oil (0.32 g, 41%). LCMS 6 min gradient method, Rt=3.6min, (M+H$^+$)=206 ii) To a solution of (S)-phenyl[(2S)-4-(phenylmethyl)morpholin-2-yl]methanethiol (6) (0.352 g, 1.18 mmole) and 2-chloro-3-phenoxypyridine (0.29 g, 1.41 mmole) in dry, degassed DMF (3 ml) is added, under nitrogen, cesium fluoride (0.179 g, 1.18 mmole). The mixture is left to stir for two days at 55° C. A further portion of cesium fluoride (0.063 g, 0.41 mmole) is added and the solution heated for 5 hours at 55° C. The reaction mixture is allowed to cool then loaded neat onto a 35 g SiO$_2$ Redisep column (preconditioned with cyclohexane). Automated flash chromatography (ISCO System, 0-40% ethyl acetate in cyclohexane gradient elution over 40 minutes at 30 ml/minute flow rate) yields a yellow oil (2.26 g). This is taken up in MeOH and loaded onto an SC10-2 column. The SC10-2 column is washed with methanol. The title compound is eluted with 2 N NH$_3$/methanol. This is 5 concentrated in vacuo to give (2S)-2-{(S)-phenyl[(3-phenyloxypyridin-2-yl)thio]methyl}-4-(phenylmethyl)morpholine as a pale orange oil (0.092 g, 17%). LCMS 6 min gradient method, Rt=3.6 min, (M+H$^+$)=469 iii) Deprotection of the morpholine nitrogen is carried out using the method and work up as described in Example 1, using polymer supported diisopropylamine (3.78 mmole/g, 0.26 g, 0.98 mmole), (2S)-2-{(S)-phenyl[(3-phenyloxypyridin-2-yl)thio]methyl}-4-(phenylmethyl)morpholine (0.092 g, 0.20 mmole), dry DCM (5 ml), 1-chloroethyl chloroformate (0.11 ml, 0.98 mmole) and methanol (5 ml). This gave (2S)-2-((S)-phenyl{[3-(phenyloxy)pyridin-2-yl]thio}methyl)morpholine as a pale yellow oil (0.070 g, 95%). This oil is taken up in ethyl acetate. To this is added a solution of fumaric acid (1.1 equiv, 0.024 g) in methanol. The resulting solution is concentrated in vacuo and the resulting oil triturated with ethyl acetate. The solid is collected by filtration to give the fumarate salt of (2S)-2-((S)-phenyl{[3-(phenyloxy)pyridin-2-yl]thio}methyl)morpholine (1:1 fumarate salt) as an off-white solid (0.094 g). LCMS 12 min gradient method, Rt=5.5 min, (M+H$^+$)=379

Example 8

(2S)-2-[(S)-[(3-chloropyridin-2-yl)thio](phenyl)methyl]morpholine fumarate

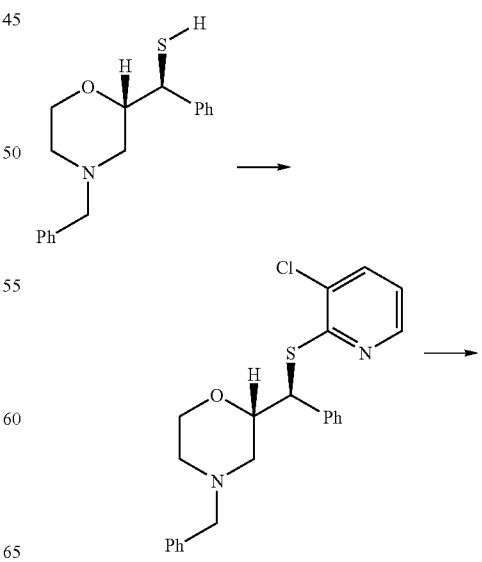

-continued

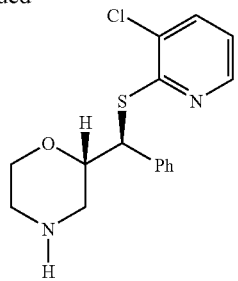

Fumarate salt i) To a solution of (S)-phenyl[(2S)-4-(phenylmethyl)morpholin-2-yl]methanethiol (6) (0.446 g, 1.49 mmole) and 2,3-dichloropyridine (0.246 g, 1.67 mmole) in dry, degassed DMF (3 ml) is added, under nitrogen, sodium hydride (60% dispersion in oil, 0.061 g, 1.53 mmole). The mixture is left to stir overnight at room temperature. The reaction mixture is taken up in MeOH and loaded onto an SC10-2 column. The SC10-2 column is washed with methanol. The (2S)-2-[(S)-[(3-chloropyridin-2-yl)thio](phenyl)methyl]-4-(phenylmethyl)morpholine is eluted with 2 N NH$_3$/methanol. This is concentrated in vacuo to give (2S)-2-[(S)-[(3-chloropyridin-2-yl)thio](phenyl)methyl]-4-(phenylmethyl)morpholine as a pale yellow oil (0.61 g). LCMS 6 min gradient method, Rt=3.5 min, (M+H$^+$)=411 ii) Deprotection of the morpholine nitrogen is carried out using the method and work up as described in Example 1, using polymer supported diisopropylamine (3.78 mmole/g, 0.39 g, 1.46 mmole), (2S)-2-[(S)-[(3-chloropyridin-2-yl)thio](phenyl)methyl]-4-(phenylmethyl)morpholine (0.120 g, 0.292 mmole), dry DCM (15 ml), 1-chloroethyl chloroformate (0.16 ml, 1.46 mmole) and methanol (15 ml). This gives (2S)-2-[(S)-[(3-chloropyridin-2-yl)thio](phenyl)methyl]morpholine as a pale yellow oil (0.092 g, 98%). This oil is taken up in ethyl acetate. To this is added a solution of fumaric acid (1 equiv, 0.033 g) in methanol. The resulting solution is concentrated in vacuo to give an oil which is crystallised from IPA. The solid is collected by filtration to give the fumarate salt of (2S)-2-[(S)-[(3-chloropyridin-2-yl)thio](phenyl)methyl]morpholine (1:1 fumarate salt) as a white solid (0.111 g). LCMS 12 min gradient method, Rt=4.8 min, (M+H$^+$)=321

Example 9

(2S)-2-[(S)-[(3-methylpyridin-2-yl)thio](phenyl)methyl]morpholine fumarate

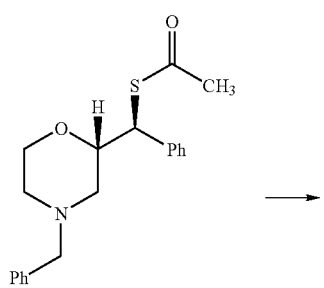

-continued

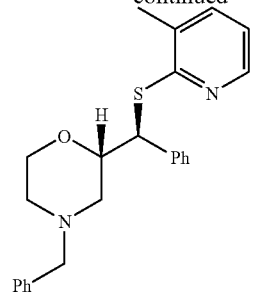

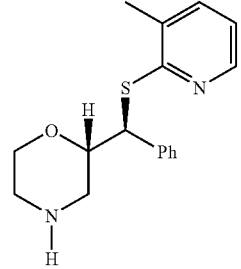

Fumarate salt i) To a degassed solution of S-{(S)-phenyl[(2S)-4-(phenylmethyl)morpholin-2-yl]methyl}ethanethioate (5) (0.100 g, 0.293 mmole) and 2-fluoro-3-methylpyridine (0.325 g, 2.93 mmole) in DMF (1 ml) is added sodium methoxide (0.016 g, 0.293 mmole). The reaction mixture is left to stir at room temperature, under nitrogen, overnight. The reaction mixture is diluted with methanol and loaded onto an SC10-2 (5 g) column preconditioned with MeOH. The column is washed with MeOH then basic material is eluted with 2 N NH$_3$/methanol. This ammonia solution is concentrated in vacuo to give an orange oil (0.067 g) which is purified by automated flash chromatography (ISCO System, Redisep SiO$_2$ column, 0-20% ethyl acetate in cyclohexane gradient elution over 40 minutes) to give (2S)-2-[(S)-[(3-methylpyridin-2-yl)thio](phenyl)methyl]-4-(phenylmethyl)morpholine as a colourless oil (0.055 g, 44%). LCMS 6 min gradient method, Rt=2.9 min, (M+H$^+$)=391 ii) To a suspension of polymer supported diisopropylamine (3.78 mmol/g, 0.167 g, 0.64 mmole) and (2S)-2-[(S)-[(3-methylpyridin-2-yl)thio](phenyl)methyl]-4-(phenylmethyl)morpholine (0.050 g, 0.13 mmole) in dry DCM (5 ml) is added 1-chloroethyl chloroform ate (0.070 ml, 0.64 mmole) at room temperature and under nitrogen. The mixture is heated at 40° C. for 1.5 hours. The reaction mixture is filtered and concentrated in vacuo then taken up in methanol (5 ml). The solution is left to stir at room temperature for 2.5 hours. After this time, the reaction mixture is loaded directly onto an SC10-2 column. The SC10-2 column is washed with methanol. The free base of the title compound is eluted with 2 N NH$_3$/methanol. This ammonia solution is concentrated in vacuo to give (2S)-2-[(S)-[(3-methylpyridin-2-yl)thio](phenyl)methyl]morpholine as an orange oil (0.037. g, 97%). This oil is taken up in methanol. To this is added a solution of fumaric acid (1 equiv, 0.014 g) in methanol. This is stirred for a couple of minutes, then EtOAc followed by isohexane added. The resulting precipitate is collected by filtration to yield a white solid (0.048 g). This is recrystallised from ethyl acetate and isohexane to give the fumarate salt of (2S)-2-[(S)-[(3-methylpyridin-2-yl)thio](phenyl)methyl]morpholine (1:1 fumarate salt) as a white solid (0.013 g) LCMS 12 min gradient method, Rt=4.5 min, (M+H⁺)=301

Example 10

(2S)-2-[(S)-{[3-(4-chlorophenyl)pyridin-2-yl]thio}(phenyl)methyl]morpholine fumarate

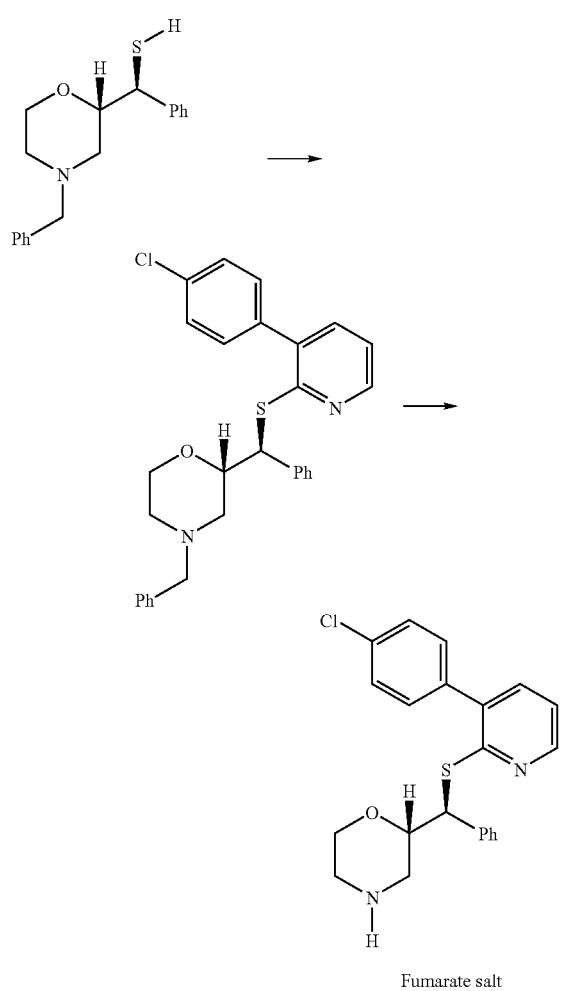

Fumarate salt i) To bis(benzonitrile)palladium(II)dichloride (0.054 g, 0.14 mmole) and 1,4-bis(diphenylphosphine)butane (0.091 g, 0.21 mmole) is added dry toluene (6 ml), under nitrogen, and the mixture stirred for half an hour. To this is added 3-bromo-2-fluoropyridine (0.50 g, 2.83 mmole) in ethanol (1.4 ml) followed by a solution of 4-chlorophenylboronic acid (0.887 g, 5.67 mmole) in ethanol (2.4 ml). To this is added an aqueous solution of sodium carbonate (1 M, 2.83 ml, 2.83 mmole). The mixture is heated at 60° C. for 24 hours, then at 75° C. for a further 16 hours. The organic layer is loaded directly onto a 40 g Redisep SiO₂ column and components isolated by automated flash chromatography (ISCO System, 0-30% ethyl acetate in cyclohexane gradient elution over 40 minutes). This gave 3-(4-chlorophenyl)-2-fluoropyridine as a white solid (0.323 g, 55%). LCMS 6 min gradient method, Rt=4.0 min, (M+H⁺)=208 ii) To a solution of (S)-phenyl[(2S)-4-(phenylmethyl)morpholin-2-yl]methanethiol (6) (0.388 g, 1.30 mmole) and 3-(4-chlorophenyl)-2-fluoropyridine (0.323 g, 1.56 mmole) in dry, degassed DMF (3 ml) is added, under nitrogen, cesium fluoride (0.295 g, 1.94 mmole). The mixture is heated at 65° C. over the weekend. After this time, the reaction mixture is allowed to cool. The resulting solid is taken up in MeOH/DCM and loaded directly onto an SC10-2 column. The SC10-2 column is washed with methanol followed by 2 N NH₃/methanol. The ammonia solution is concentrated in vacuo to give (2S)-2-[(S)-{[3-(4-chlorophenyl)pyridin-2-yl]thio}(phenyl)methyl]-4-(phenylmethyl)morpholine as an orange foam (0.514 g). This is purified by automated flash chromatography (ISCO System, 0-30% ethyl acetate in cyclohexane gradient elution over 40 minutes at 40 ml/minute flow rate) to give (2S)-2-[(S)-{[3-(4-chlorophenyl)pyridin-2-yl]thio}(phenyl)methyl]-4-(phenylmethyl)morpholine as a white foam (0.178 g, 28%). LCMS 6 min gradient method, Rt=4.2 min, (M+H⁺)=487 iii) Deprotection of the morpholine nitrogen is carried out using the method and work up as described in Example 1, using polymer supported diisopropylamine (3.78 mole/g, 0.48 g, 1.80 mmole), (2S)-2-[(S)-{[3-(4-chlorophenyl)pyridin-2-yl]thio}(phenyl)methyl]-4-(phenylmethyl)morpholine (0.175 g, 0.36 mmole), dry DCM (10 ml), 1-chloroethyl chloroformate (0.20 ml, 1.80 mmole) and methanol (10 ml). This gave a colourless residue (0.129 g, 90%). This residue is taken up in ethyl acetate. To this is added a solution of fumaric acid (1.1 equiv, 0.035 g) in methanol. The resulting solid is recombined with the mother liquor and purified on a UV Guided PrepHPLC (Flex) System and treated with SC10-2 to give a yellow solid. This is further purified by automated flash chromatography (ISCO System, Redisep 4 g SiO₂ column, 0-5% methanol in dichloromethane gradient elution over 40 minutes, then 10 minutes at 5% Methanol in dichloromethane with 10 ml/min flow rate) to give (2S)-2-[(S)-{[3-(4-chlorophenyl)pyridin-2-yl]thio}(phenyl)methyl]morpholine as a pale yellow oil (0.049 g, 34%). This oil is taken up in ethyl acetate. To this is added a solution of fumaric acid (1.1 equiv, 0.0145 g) in methanol. The resulting solution is concentrated in vacuo and recrystallised from MeOH and Et₂O. The solid is collected by filtration to give the fumarate salt of (2S)-2-[(S)-{[3-(4-chlorophenyl)pyridin-2-yl]thio}(phenyl)methyl]morpholine (1:1 fumarate salt) as a white solid (0.047 g). LCMS 12 min gradient method, Rt=5.7 min, (M+H⁺)=397

Example 11

(2S)-2-[(S)-[(5-bromopyridin-2-yl)thio](phenyl)methyl]morpholine fumarate

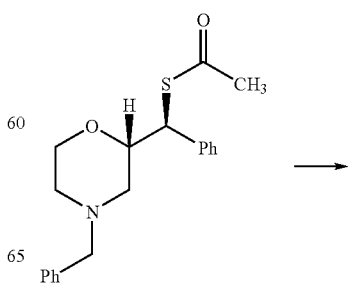

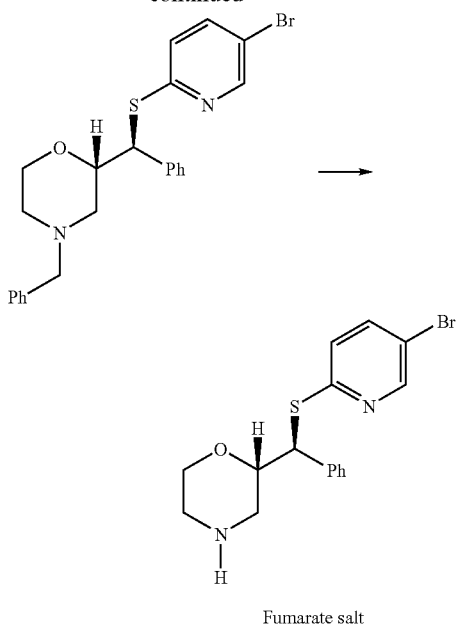

i) To a solution of S-{(S)-phenyl[(2S)-4-(phenylmethyl)morpholin-2-yl]methyl}ethanethioate (5) (0.25 g, 0.73 mmole) in dry methanol (2 ml) is added sodium methoxide (0.040 g, 0.73 mmole) under nitrogen. This is left to stir at room temperature for 1 hour. Methanol is removed in vacuo and replaced with DMF (1 ml). To this is then added the 5-bromo-2-fluoropyridine (0.11 ml, 1.02 mmole). The reaction mixture is left to stir at room temperature, under nitrogen, overnight. The reaction mixture is diluted with DCM and loaded directly onto a 35 g Redisep column. Purification by automated flash chromatography (ISCO System, Redisep 35 g SiO$_2$ column, 0-20% ethyl acetate in cyclohexane gradient elution over 40 minutes) gave (2S)-2-[(S)-[(5-bromopyridin-2-yl)thio](phenyl)methyl]-4-(phenylmethyl)morpholine as a colourless oil (0.186 g, 56%). LCMS 6 min gradient method, Rt=3.6 min, (M+H$^+$)=455/457 ii) To a suspension of polymer supported diisopropylamine (3.78 mmol/g, 0.108 g, 20.4 mmole) and (2S)-2-[(S)-[(5-bromopyridin-2-yl)thio](phenyl)methyl]-4-(phenylmethyl)morpholine (0.186 g, 0.408 mmole) in dry DCM (10 ml) is added 1-chloroethyl chloroformate (0.22 ml, 2.04 mmole) at room temperature and under nitrogen. The mixture is heated at 40° C. for 2.5 hours. The reaction mixture is then filtered and concentrated in vacuo then taken up in methanol (10 ml). The solution is left to stir at room temperature overnight. After this time, the reaction mixture is loaded directly onto an SC10-2 column (5 g). The SC10-2 column is washed with methanol. The target compound is eluted with 2 N NH$_3$/methanol. This is concentrated in vacuo to give (2S)-2-[(S)-[(5-bromopyridin-2-yl)thio](phenyl)methyl]morpholine as a colourless oil (0.108. g, 72%). This oil is taken up in ethanol. To this is added a solution of fumaric acid (1.2 equiv, 0.041 g) in ethanol. Solvent is removed in vacuo and the resulting residue triturated with EtOAc. This solid is collected by filtration to give the fumarate salt of (2S)-2-[(S)-[(5-bromopyridin-2-yl)thio](phenyl)methyl]morpholine (1:1 fumarate salt) as a white solid (0.105 g). LCMS 12 min gradient method, Rt=5.0 min, (M+H$^+$)=365/367

Example 12

2-{[(S)-(2S)-morpholin-2-yl(phenyl)methyl]thio}pyridine-3-carboxamide fumarate

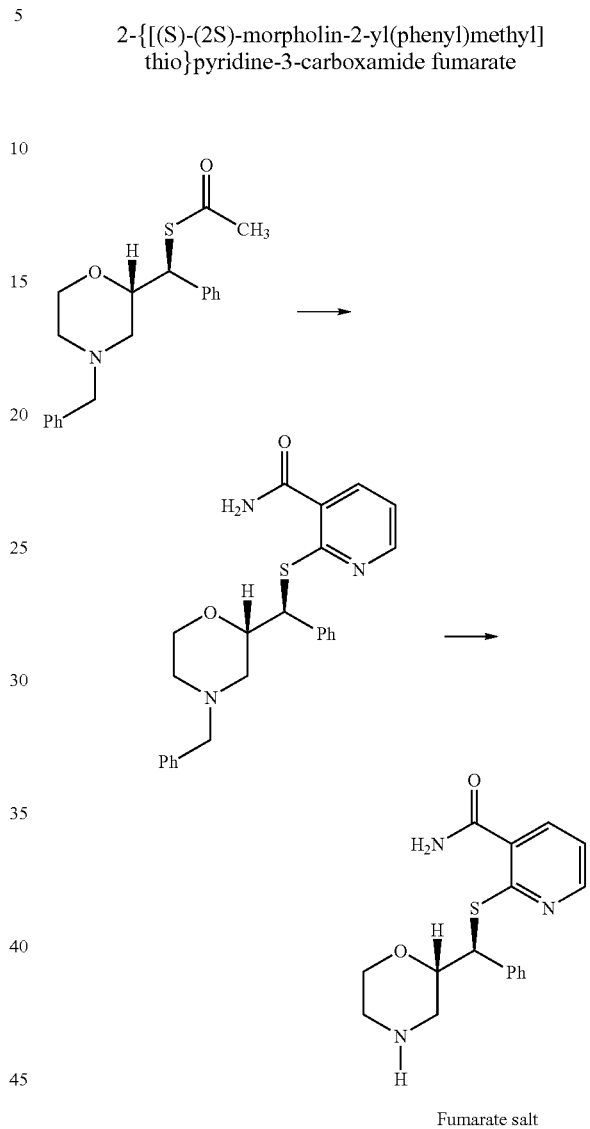

i) To a degassed solution of S-{(S)-phenyl[(2S)-4-(phenylmethyl)morpholin-2-yl]methyl}ethanethioate (5) (0.100 g, 0.293 mmole) and 2-chloronicotinamide (0.046 g, 0.293 mmole) in ethanol (3 ml) is added a solution of sodium hydroxide in water (2 M, 0.293 ml, 0.586 mmole). The resulting solution is stirred at room temperature overnight. An additional portion of 2-chloronicotinamide (0.046 g, 0.293 mmole) is added to the reaction mixture which is then heated at 40° C. overnight. The reaction mixture is diluted with methanol and loaded onto an SC10-2 column preconditioned with MeOH. The column is washed with MeOH then basic material is eluted with 2 N NH$_3$/methanol. This ammonia solution is concentrated in vacuo to give 2-({[(S)-phenyl[(2S)-4-(phenylmethyl)morpholin-2-yl]methyl}thio)pyridine-3-carboxamide as a pale orange residue (0.124 g, 100%). LCMS 6 min gradient method, Rt=2.1 min, (M+H$^+$)=420 ii) To a suspension of polymer supported diisopropylamine (3.78 mmol/g, 0.38 g, 1.47 mmole) and 2-({[(S)-phenyl[(2S)-

4-(phenylmethyl)morpholin-2-yl]methyl}thio)pyridine-3-carboxamide (0.123 g, 0.29 mmole) in dry DCM (10 ml) is added 1-chloroethyl chloroformate (0.16 ml, 1.47 mmole) at room temperature and under nitrogen. The mixture is heated at 40° C. for 2 hours. The reaction mixture is then filtered and concentrated in vacuo to give a pale yellow residue. This is taken up in methanol (10 ml) and the solution left to stir at room temperature for 3 hours. After this time, the reaction mixture is loaded directly onto an SC10-2 column. The SC10-2 column is washed with methanol then more basic compounds are eluted with 2 N NH₃/methanol. The ammonia soluition is concentrated in vacuo to give 2-{[(S)-(2S)-morpholin-2-yl(phenyl)methyl]thio}pyridine-3-carboxamide as a pale yellow oil (0.097 g, 100%). The pale yellow oil is taken up in methanol. To this is added a solution of fumaric acid (1 equiv, 0.0153 g) in methanol. This is stirred for a couple of minutes, then EtOAc added. The resulting precipitate is collected by filtration to give the fumarate salt of 2-{[(S)-(2S)-morpholin-2-yl(phenyl)methyl]thio}pyridine-3-carboxamide (1:1 fumarate salt) as a white solid (0.095 g). LCMS 12 min gradient method, Rt=2.4 min, (M+H⁺)=330

Example 13

2-{[(S)-(2S)-morpholin-2-yl(phenyl)methyl]thio}pyridine-3-carbonitrile fumarate

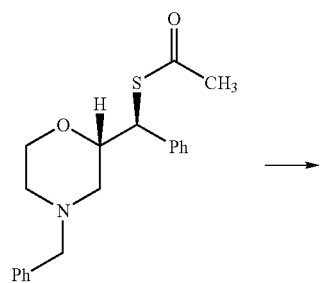

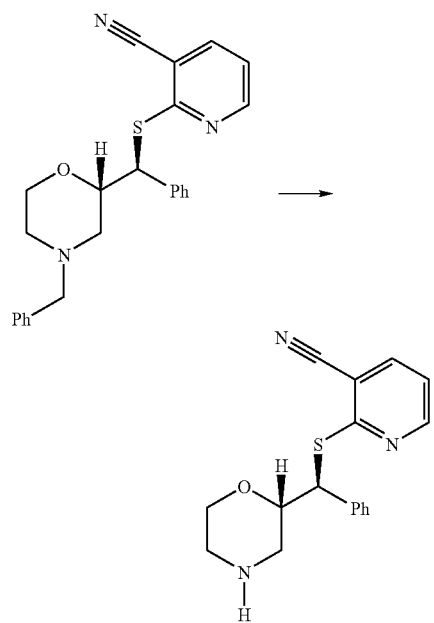

i) To a degassed solution of S-{(S)-phenyl[(2S)-4-(phenylmethyl)morpholin-2-yl]methyl}ethanethioate (5) (0.050 g, 0.147 mmole) and 2-chloro-3-cyanopyridine (0.020 g, 0.146 mmol) in ethanol (1.5 ml) is added a solution of sodium hydroxide in water (2 M, 0.146 ml, 0.293 mmole). The resulting solution is stirred at room temperature for ~17 hours. The reaction mixture is diluted with methanol and loaded onto an SC10-2 column preconditioned with MeOH. The column is washed with MeOH then basic material is eluted with 2 N NH₃/methanol. This ammonia solution is concentrated in vacuo to give 2-({[(S)-phenyl[(2S)-4-(phenylmethyl)morpholin-2-yl]methyl}thio)pyridine-3-carbonitrile as an off white solid (0.055 g, 93%). LCMS 6 min gradient method, Rt=2.8 min, (M+H⁺)=402 ii) To a suspension of polymer supported diisopropylamine (3.78 mmol/g, 0.181 g, 0.685 mmole) and 2-({[(S)-phenyl[(2S)-4-(phenylmethyl)morpholin-2-yl]methyl}thio)pyridine-3-carbonitrile (0.055 g, 0.137 mmole) in dry DCM (5 ml) is added 1-chloroethyl chloroformate (0.075 ml, 0.685 mmole) at room temperature and under nitrogen. The mixture is heated at 40° C. for 2 hours. The reaction mixture is then filtered and concentrated in vacuo to give a pale orange liquid. This is taken up in methanol (5 ml) and the solution left to stir at room temperature overnight. After this time, the reaction mixture is loaded directly onto an SC10-2 column. The SC10-2 column is washed with methanol then more basic material is eluted with 2 N NH₃/methanol. The ammonia solution is concentrated in vacuo to give 2-{[(S)-(2S)-morpholin-2-yl(phenyl)methyl]thio}pyridine-3-carbonitrile as a pale yellow oil (0.041 g, 95%). The pale yellow oil is taken up in methanol. To this is added a solution of fumaric acid (1 equiv, 0.0153 g) in methanol. This is stirred for a couple of minutes, then EtOAc followed by cyclohexane added. The resulting precipitate is collected by filtration to give the fumarate salt of 2-{[(S)-(2S)-morpholin-2-yl(phenyl)methyl]thio}pyridine-3-carbonitrile (1:1 fumarate salt) as a white solid (0.042 g). LCMS 12 min gradient method, Rt=4.6 min, (M+H⁺)=312

Example 14

(2S)-2-[phenyl(pyridin-2-ylthio)methyl]morpholine hydrochloride

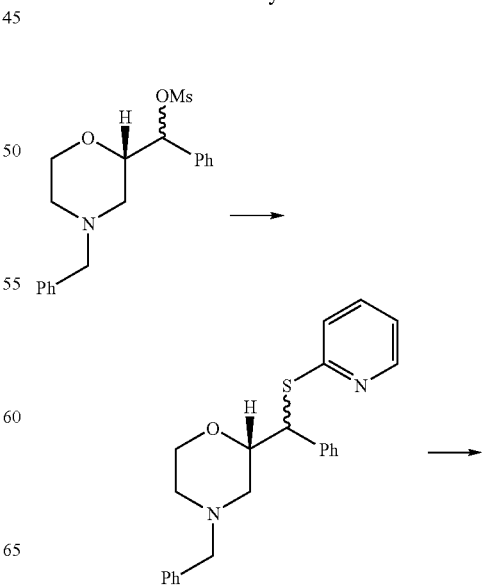

45

-continued

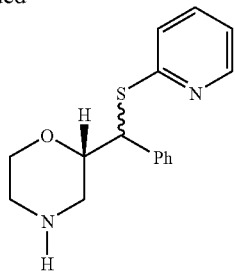

Fumarate salt i) To a stirred solution of (R)-phenyl[(2S)-4-(phenylmethyl)morpholin-2-yl]methyl methanesulfonate (0.70 g, 1.94 mmole) and 2-mercaptopyridine (0.54 g, 4.84 mmole) in anhydrous DMF, at room temperature and under nitrogen, is added potassium carbonate (0.80 g, 5.81 mmole). The reaction is left to stir at room temperature for 6 days. The reaction mixture is diluted with methanol and loaded onto an SC10-2 column preconditioned with MeOH. The column is washed with MeOH then basic material is eluted with 2 N $NH_3$/methanol. This ammonia solution is concentrated in vacuo to give an orange residue (0.881 g). Purification by automated flash chromatography (ISCO System, 0-30% ethyl acetate in isohexane gradient elution over 30 minutes) gave (2S)-2-[phenyl(pyridin-2-ylthio)methyl]-4-(phenylmethyl)morpholine as a colourless oil (0.245 g, 34%). LCMS 6 min gradient method, Rt=2.7 min, $(M+H^+)$=377.

ii) Deprotection of the morpholine nitrogen is carried out using the method and work up as described in Example 1, using polymer supported diisopropylamine (3.78 mmole/g, 0.43 g, 1.64 mmole), (2S)-2-[phenyl(pyridin-2-ylthio)methyl]-4-(phenylmethyl)morpholine (0.103g, 0.274 mmole), dry DCM (10 ml), 1-chloroethyl chloroformate (0.15 ml, 1.37 mmole) and methanol (10 ml). This gave a pale yellow oil (0.058 g, 74%). ). Purification of this residue by automated flash chromatography (ISCO System, $SiO_2$ Redisep column, 10% MeOH in DCM) gave a colourless oil (0.044 g, 54%). This oil is taken up in ethyl acetate. To this is added a solution of hydrochloric acid in dioxane (4 M, 0.1 ml). Concentration in vacuo gave the hydrochloride salt of (2S)-2-[phenyl(pyridin-2-ylthio)methyl] as a white solid (0.045 g). LCMS 6 min gradient method, Rt=1.8 min, $(M+H^+)$=287

Example 15

(2S)-2-[(S)-[(3-iodopyridin-2-yl)thio](phenyl)methyl]morpholine fumarate

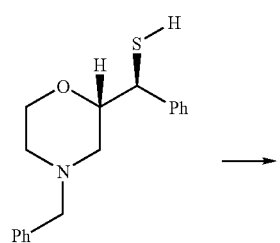

46

-continued

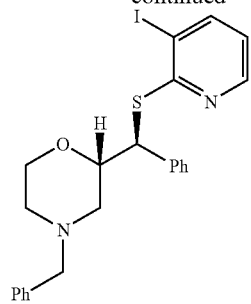

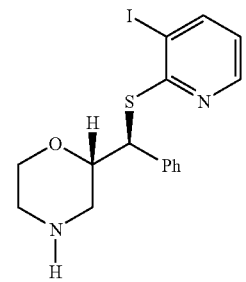

Fumarate salt i) To (S)-phenyl[(2S)-4-(phenylmethyl)morpholin-2-yl] methanethiol (6) (0.50 g, 1.67 mmole) and 2-chloro-3-iodopyridine (0.48 g, 2.00 mmole) in degassed DMF (3 ml) is added cesium fluoride (0.38 g, 2.50 mmole) at room temperature and under nitrogen. The mixture is heated at between 55-75° C. for 3 days. The organic layer is then loaded directly onto a 35 g ISCO column ($SiO_2$) and columned using automated flash chromatography (0-30% EtOAc in cyclohexane over 30 minutes) to give a pale yellow crystalline solid (0.55 g). The solid is taken up in DCM:MeOH (1:1) and loaded onto an SC10-2 column (10 g) preconditioned with MeOH. The column is washed with MeOH to remove 2-chloro-3-iodopyridine, then more basic material is eluted with 2 N $NH_3$/methanol. The ammonia solution is concentrated in vacuo to give (2S)-2-[(S)-[(3-iodopyridin-2-yl)thio](phenyl)methyl]-4-(phenylmethyl)morpholine as a pale yellow solid (0.19 g, 23%). LCMS 6 min gradient method, Rt=3.8 min, $(M+H^+)$=503 ii) To a suspension of polymer supported diisopropylamine (3.72 mmol/g, 0.285 g, 1.06 mmole) and (2S)-2-[(S)-[(3-iodopyridin-2-yl)thio](phenyl)methyl]-4-(phenylmethyl) morpholine (0.107 g, 0.21 mmole) in dry DCM (1.5 ml) is added 1-chloroethyl chloroformate (0.116 ml, 1.06 mmole) at room temperature and under nitrogen. The mixture is heated at 40° C. for 2 hours. The reaction mixture is then filtered and concentrated in vacuo to give a pale orange liquid. This is taken up in methanol (1.5 ml) and the solution left to stir at room temperature overnight. After stirring overnight at room temperature, the reaction mixture is loaded directly onto an SC10-2 column. The SC10-2 column is washed with methanol, then more basic material is eluted with 2 N $NH_3$/methanol. The ammonia solution is concentrated in vacuo to give (2S)-2-[(S)-[(3-iodopyridin-2-yl)thio](phenyl)methyl]morpholine as a pale yellow oil (0.047 g, 53%). This oil is taken up in methanol and to this is added a solution of fumaric acid (1 equiv, 0.013 g) in methanol. This is stirred for a couple of minutes, then EtOAc followed by $Et_2O$ added. The resulting precipitate is collected by filtration to give the fumarate salt of (2S)-2-[(S)-[(3-iodopyridin-2-yl)thio](phenyl)methyl]morpholine (1:1 fumarate salt) as a white solid (0.036 g). LCMS 12 min gradient method, Rt=4.9 min, (M+H⁺)=413

The pharmacological profile of the present compounds may be demonstrated as follows. All of the exemplified compounds above have been found to exhibit a $K_i$ value less than 500 nM at the norepinephrine transporter as determined using the scintillation proximity assay described below. Furthermore, all of the exemplified compounds above have been found to selectively inhibit the norepinephrine transporter relative to the serotonin and dopamine transporters by a factor of at least five using the scintillation proximity assays as described below.

Generation of Stable Cell-Lines Expressing the Human Dopamine, Norepinephrine and Serotonin Transporters Standard molecular cloning techniques are used to generate stable cell-lines expressing the human dopamine, norepinephrine and serotonin transporters. The polymerase chain reaction (PCR) is used in order to isolate and amplify each of the three full-length cDNAs from an appropriate cDNA library. Primers for PCR are designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganapathy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products are cloned into a mammalian expression vector (eg pcDNA3.1 (Invitrogen)) using standard ligation techniques. The constructs are then used to stably transfect HEK293 cells using a commercially available lipofection reagent (Lipofectamine™—Invitrogen) following the manufacture's protocol.

Scintillation Proximity Assays for Determining the Affinity of Test Ligands at the Monoamine Transporters.

Norepinephrine Binding Assay

The compounds of the present invention are norepinephrine reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus ³H-nisoxetine binding to norepinephrine reuptake sites in a cell line transfected with DNA encoding human norepinephrine transporter binding protein has been used to determine the affinity of ligands at the norepinephrine transporter.

Membrane Preparation:

Cell pastes from large scale production of HEK-293 cells expressing cloned human norepinephrine transporters are homogenized in 4 volumes 50 mM Tris-HCl containing 300 mM NaCl and 5 mM KCl, pH 7.4. The homogenate is centrifuged twice (40,000 g, 10 min, 4° C.) with pellet re-suspension in 4 volumes of Tris-HCl buffer containing the above reagents after the first spin and 8 volumes after the second spin. The suspended homogenate is centrifuged (100 g, 10 min, 4° C.) and the supernatant kept and re-centrifuged (40, 000 g, 20 min, 4° C.). The pellet is resuspended in Tris-HCl buffer containing the above reagents along with 10% w/v sucrose and 0.1 mM phenylmethylsulfonyl fluoride (PMSF). The membrane preparation is stored in aliquots (1 ml) at −80° C. until required. The protein concentration of the membrane preparation is determined using a bicinchoninic acid (BCA) protein assay reagent kit (available from Pierce).

[³H]-Nisoxetine Binding Assay:

Each well of a 96 well microtitre plate is set up to contain the following:

| | |
|---|---|
| 50 µl | 2 nM [N-methyl-³H]-Nisoxetine hydrochloride (70-87 Ci/mmol, from NEN Life Science Products) |
| 75 µl | Assay buffer (50 mM Tris-HCl pH 7.4 containing 300 mM NaCl and 5 mM KCl) |
| 25 µl | Test compound, assay buffer (total binding) or 10 µM Desipramine HCl (non-specific binding) |
| 50 µl | Wheatgerm agglutinin coated poly(vinyltoluene) (WGA PVT) SPA Beads (Amersham Biosciences RPNQ0001) (10 mg/ml) |
| 50 µl | Membrane (0.2 mg protein per ml) |

The microtitre plates are incubated at room temperature for 10 hours prior to reading in a Trilux scintillation counter. The results are analysed using an automatic spline fitting programme (Multicaic, Packard, Milton Keynes, UK) to provide $K_i$ values for each of the test compounds.

Serotonin Binding Assay

The ability of a test compound to compete with [³H]-citalopram for its binding sites on cloned human serotonin transporter containing membranes has been used as a measure of test compound ability to block serotonin uptake via its specific transporter (Ramamoorthy, S., Giovanetti, E., Qian, Y., Blakely, R., (1998) J. Biol. Chem. 273, 2458).

Membrane Preparation:

Membrane preparation is essentially similar to that for the norepinephrine transporter containing membranes as described above. The membrane preparation is stored in aliquots (1 ml) at −70° C. until required. The protein concentration of the membrane preparation is determined using a BCA protein assay reagent kit.

[³H]-Citalopram Binding Assay:

Each well of a 96 well microtitre plate is set up to contain the following:

| | |
|---|---|
| 50 µl | 2 nM [³H]-Citalopram (60-86 Ci/mmol, Amersham Biosciences) |
| 75 µl | Assay buffer (50 mM Tris-HCl pH 7.4 containing 150 mM NaCl and 5 mM KCl) |
| 25 µl | Diluted compound, assay buffer (total binding) or 100 µM Fluoxetine (non-specific binding) |
| 50 µl | WGA PVT SPA Beads (40 mg/ml) |
| 50 µl | Membrane preparation (0.4 mg protein per ml) |

The microtitre plates are incubated at room temperature for 10 hours prior to reading in a Trilux scintillation counter. The results are analysed using an automatic spline fitting programme (Multicalc, Packard, Milton Keynes, UK) to provide Ki (nM) values for each of the test compounds.

Dopamine Binding Assay

The ability of a test compound to compete with [³H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[3H]-WIN35,428 Binding Assay:

Each well of a 96well microtitre plate is set up to contain the following:

| | |
|---|---|
| 50 μl | 4 nM [³H]-WIN35, 428 (84-87 Ci/mmol, from NEN Life Science Products) |
| 75 μl | Assay buffer (50 mM Tris-HCl pH 7.4 containing 150 mM NaCl and 5 mM KCl) |
| 25 μl | Diluted compound, assay buffer (total binding) or 100 μM Nomifensine (non-specific binding) |
| 50 μl | WGA PVT SPA Beads (10 mg/ml) |
| 50 μl | Membrane preparation (0.2 mg protein per ml.) |

The microtitre plates are incubated at room temperature for 120 minutes prior to reading in a Trilux scintillation counter. The results are analysed using an automatic spline fitting programme (Multicalc, Packard, Milton Keynes, UK) to provide Ki values for each of the test compounds.

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme exhibits genetic polymorphism, resulting in the presence of both poor and normal metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) are acquired from Human Biologics (Scottsdale, Ariz., USA). Quinidine and β-NADPH (β-Nicotinamide Adenine Dinucleotide Phosphate, reduced form, tetrasodium salt) are purchased from Sigma (St Louis, Mo., USA). All the other reagents and solvents are of analytical grade. A stock solution of the new chemical entity (NCE) is prepared in a mixture of Acetonitrile/Water to reach a final concentration of acetonitrile in the incubation below 0.5%.

The microsomal incubation mixture (total volume 0.1 mL) contained the NCE (4 μM), μ-NADPH (1 mM), microsomal proteins (0.5 mg/mL), and Quinidine (0 or 2 μM) in 100 mM sodium phosphate buffer pH 7.4. The mixture is incubated for 30 minutes at 37° C. in a shaking waterbath. The reaction is terminated by the addition of acetonitrile (75 μL). The samples are vortexed and the denaturated proteins are removed by centrifugation. The amount of NCE in the supernatant is analyzed by liquid chromatography/mass spectrometry (LC/MS) after addition of an internal standard. A sample is also taken at the start of the incubation (t=0), and analysed similarly.

Analysis of the NCE is performed by liquid chromatography/mass spectrometry. Ten μL of diluted samples (20 fold dilution in the mobile phase) are injected onto a Spherisorb CN Column, 5 μM and 2.1 mm×100 mm (Waters corp. Milford, Mass., USA). The mobile phase consisting of a mixture of Solvent A/Solvent B, 30/70 (v/v) is pumped (Alliance 2795, Waters corp. Milford, Mass., USA) through the column at a flow rate of 0.2 ml/minute. Solvent A and Solvent B are a mixture of ammonium formate $5.10^{-3}$ M pH 4.5/methanol in the proportions 95/5 (v/v) and 10/90 (v/v), for solvent A and solvent B, respectively. The NCE and the internal standard are quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) is calculated comparing the extent of metabolism in absence and in presence of quinidine in the incubation.

The extent of metabolism without inhibitor (%) is calculated as follows:

$$\frac{(NCE \text{ response in samples without inhibitor}) \text{ time } 0 - (NCE \text{ response in samples without inhibitor}) \text{ time } 30}{(NCE \text{ response in samples without inhibitor}) \text{ time } 0} \times 100$$

The extent of metabolism with inhibitor (%) is calculated as follows:

$$\frac{(NCE \text{ response in samples without inhibitor}) \text{ time } 0 - (NCE \text{ response in samples without inhibitor}) \text{ time } 30}{(NCE \text{ response in samples without inhibitor}) \text{ time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement is calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 μM for CYP2D6 activity, the $IC_{50}$ being the concentration of the compound that gives 50% of inhibition of the CYP2D6 activity.

Material and Methods:

Human liver microsomes (mixture of 20 different donors, mixed gender) are acquired from Human Biologics (Scottsdale, Ariz.). β-NADPH is purchased from Sigma (St Louis, Mo.). Bufuralol is purchased from Ultrafine (Manchester, UK). All the other reagents and solvents are of analytical grade.

Microsomal incubation mixture (total volume 0.1 mL) contained bufuralol 10 µM, β-NADPH (2 mM), microsomal proteins (0.5 mg/mL), and the new chemical entity (NCE) (0, 5, and 25 µM) in 100 mM sodium phosphate buffer pH 7.4. The mixture is incubated in a shaking waterbath at 37° C. for 5 minutes. The reaction is terminated by the addition of methanol (75 µL). The samples are vortexed and the denaturated proteins are removed by centrifugation. The supernatant is analyzed by liquid chromatography connected to a fluorescence detector. The formation of the 1'-hydroxybufuralol is monitored in control samples (0 µM NCE) and in the samples incubated in presence of the NCE. The stock solution of NCE is prepared in a mixture of Acetonitrile/Water to reach a final concentration of acetonitrile in the incubation below 1.0%.

The determination of 1'hydroxybufuralol in the samples is performed by liquid chromatograhy with fluorimetric detection as described below. Twenty five µL samples are injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, is pumped through the column at a flow rate of 1 ml/min:

| Time (minutes) | Solvent A (%) | Solvent B (%) |
| --- | --- | --- |
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time is 7.5 minutes. Formation of 1'-hydroxybufuralol is monitored by fluorimetric detection with extinction at λ 252 nm and emission at λ 302 nm.

The $IC_{50}$ of the NCE for CYP2D6 is calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The $IC_{50}$ is calculated from the percent inhibition of the formation of the 1'-hydroxybufuralol as follows (assuming competitive inhibition):

$$\frac{NCE\,\text{Concentration} \times (100 - \text{Percent of inhibition})}{\text{Percent of inhibition}}$$

The $IC_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

Acid Stability

The acid stability of a compound according to the present invention is determined as a solution in buffer at 6 different pH values (HC1 0.1N, pH 2, pH 4, pH 6, pH 7, and pH 8) at 40° C. over a time course of 72 hours. Samples are taken at the beginning of the study and after 3, 6 and 24 hours and analysed by capillary electrophoresis. The original sample used in this study contained 0.8% of the undesired epimer as internal standard. The samples taken at the different time points during the study does not show any significant change in the percentage of the undesired epimer. This confirms that the compound is chemically and configurationally stable under acidic conditions.

The invention claimed is:

1. A compound of formula (I)

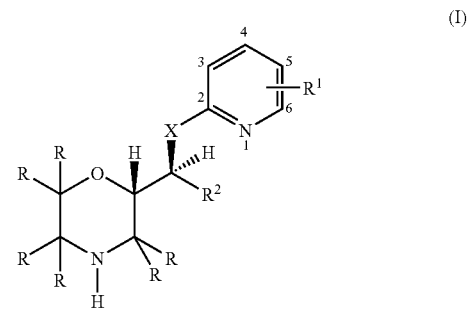

wherein
—X— is —S— or —O—;
each R is independently selected from H or $C_1$-$C_4$ alkyl;
$R^1$ is H, $C_1$-$C_4$ alkyl, $C_1$-$C_4$ alkoxy, halo, cyano, trifluoromethyl, trifluoromethoxy, —$NR^3R^4$, —$CONR^3R^4$, —$COOR^3$ or a group of the formula (i)

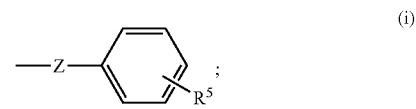

$R^2$ is $C_1$-$C_4$ alkyl, phenyl or phenyl substituted with 1, 2 or 3 substituents each independently selected from $C_1$-$C_4$ alkyl, $C_1$-$C_4$ alkoxy, nitro, hydroxy, cyano, halo, trifluoromethyl, trifluoromethoxy, benzyl, benzyloxy, —$NR^6R^7$, —$CONR^6R^7$, $COOR^6$, —$SO^2NR^6R^7$ and —$SO_2R^6$;
$R^5$ is selected from H, $C_1$-$C_4$ alkyl, $C_1$-$C_4$ alkoxy, carboxy, nitro, hydroxy, cyano, halo, trifluoromethyl, trifluoromethoxy, benzyl, benzyloxy, —NR$^8$R$^9$, —CONR$^8$R$^9$, —SO$_2$NR$^8$R$^9$ and —SO$_2$R$^8$;

R$^3$, R$^4$, R$^6$, R$^7$, R$^8$ and R$^9$ are each independently selected from H or C$_1$-C$_4$ alkyl; and -Z- is a bond, —CH$_2$—, or —O—;

or a pharmaceutically acceptable salt thereof.

2. A compound as claimed in claim 1, wherein —X— is —S—.

3. A compound as claimed in claim 1, wherein R$^2$ is phenyl.

4. A compound as claimed in claim 1, wherein all R groups are hydrogen.

5. A compound as claimed in claim 1, represented by the formula (II)

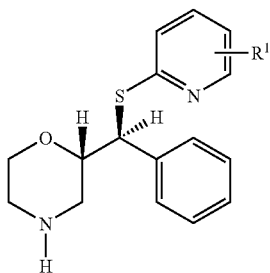

(II)

wherein R$^1$ is H, C$_1$-C$_4$ alkyl, C$_1$-C$_4$ alkoxy, halo, cyano, trifluoromethyl, trifluoromethoxy, —NR$^3$R$^4$, —CONR$^3$R$^4$, —COOR$^3$ or a group of the formula (i)

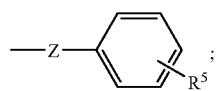

(i)

R$^5$ is selected from H, C$_1$-C$_4$ alkyl, C$_1$-C$_4$ alkoxy, carboxy, nitro, hydroxy, cyano, halo, trifluoromethyl, trifluoromethoxy, benzyl, benzyloxy, —NR$^8$R$^9$, —CONR$^8$R$^9$, —SO$_2$NR$^8$R$^9$ and —SO$_2$R$^8$;

R$^3$, R$^4$, R$^8$ and R$^9$ are each independently selected from H or C$_1$-C$_4$ alkyl;

-Z- is a bond, —CH$_2$—, or —O—;

or a pharmaceutically acceptable salt thereof.

6. A compound as claimed in claim 1, wherein the substituent R$^1$ is in the three position of the pyridine ring as numbered in formula (I) above.

7. A compound as claimed in claim 1, wherein R$^1$ is H, C$_1$-C$_4$ alkyl, halo, cyano, —CONR$^3$R$^4$, trifluoromethyl or a group of the formula (i).

8. A compound as claimed in claim 1, wherein R$^1$ is —CONR$^3$R$^4$ and R$^3$ and R$^4$ are both H.

9. A compound as claimed in claim 1, wherein R$^1$ is a group of the formula (i), -Z- is a bond, and R$^5$ is H or halo.

10. A compound as claimed in claim 1, wherein R$^1$ is a group of the formula (i), -Z- is —CH$_2$, or —O—, and R$^5$ is H.

11. A compound as claimed in claim 1, wherein the substituent R$^1$ is in the five position of the pyridine ring as numbered in formula (I) above.

12. A compound as claimed in claim 11, wherein the substituent R$^1$ is selected from bromo, chloro or iodo.

13. A pharmaceutical compositions, comprising a compound as claimed in claim 1 or a pharmaceutically acceptable salt thereof, together with a pharmaceutically acceptable diluent, excipient or carrier.

14. A method for selectively inhibiting the reuptake of norepinephrine in mammals, comprising administering to a patient in need thereof an effective amount of a compound as claimed in claim 1, or a pharmaceutically acceptable salt thereof.

15. A method for treating disorders associated with norepinephrine dysfunction in mammals selected from the group consisting of an attention-deficit disorder (ADD) due to general medical conditions, attention-deficit hyperactivity disorder (ADHD) including the predominantly inattentive type of ADHD and the predominantly hyperactive-impulsive type of ADHD, cognitive disorders including mild cognitive impairment (MCI) and cognitive impairment associated with schizophrenia (CIAS), conduct disorder, depression (including adolescent depression and minor depression), dysthymic disorder, and oppositional defiant disorder, comprising administering to a patient in need thereof an effective amount of a compound as claimed in claim 1, or a pharmaceutically acceptable salt thereof.

* * * * *